United States Patent
Holmes

(10) Patent No.: US 12,220,386 B2
(45) Date of Patent: Feb. 11, 2025

(54) PHARMACEUTICAL COUNTING AND PACKAGING DEVICE

(71) Applicant: RXSAFE LLC, Vista, CA (US)

(72) Inventor: William K. Holmes, San Diego, CA (US)

(73) Assignee: RXSAFE LLC, Vista, CA (US)

( * ) Notice: Subject to any disclaimer, the term of this patent is extended or adjusted under 35 U.S.C. 154(b) by 132 days.

(21) Appl. No.: 17/909,226

(22) PCT Filed: Mar. 2, 2021

(86) PCT No.: PCT/US2021/020529
§ 371 (c)(1),
(2) Date: Sep. 2, 2022

(87) PCT Pub. No.: WO2021/178443
PCT Pub. Date: Sep. 10, 2021

(65) Prior Publication Data
US 2023/0101967 A1    Mar. 30, 2023

Related U.S. Application Data

(60) Provisional application No. 62/984,143, filed on Mar. 2, 2020.

(51) Int. Cl.
*B65B 5/10* (2006.01)
*A61J 7/00* (2006.01)
(Continued)

(52) U.S. Cl.
CPC .............. *A61J 7/02* (2013.01); *A61J 7/0069* (2013.01); *B65B 5/103* (2013.01); *B65B 35/12* (2013.01);
(Continued)

(58) Field of Classification Search
CPC ....... B65B 35/12; B65B 57/14; B65B 57/145; B65B 57/20; B65B 9/02; B65B 5/103; B65B 2220/16; B65B 61/26
(Continued)

(56) References Cited

U.S. PATENT DOCUMENTS 5,522,512 A    6/1996  Archer et al.
5,564,593 A   10/1996  East, Sr.
(Continued)

FOREIGN PATENT DOCUMENTS

CA    2620159 C   12/2014
CA    2790220 C    6/2016
(Continued)

OTHER PUBLICATIONS

Japanese Patent Office Action for application 2020-545316, dated Jan. 4, 2023 (14 pages with translation).
(Continued)

*Primary Examiner* — Jacob A Smith
(74) *Attorney, Agent, or Firm* — Michael Best & Friedrich LLP

(57) ABSTRACT

One embodiment provides a pharmaceutical counting device (160, 800) including a base portion (810) and a counting tray (830) provided on the base portion (810). The counting tray (830) is tilted about a first axis to empty medications into a first package and tiled above a second axis to empty medications into a second package. The pharmaceutical counting device (160, 800) also includes a camera system (950) to capture images of the counting tray (830), the packages, and a label on the packages. The pharmaceutical counting device (160, 800) verifies whether a correct number and type of medications are received on the counting tray (830).

8 Claims, 26 Drawing Sheets

(51) Int. Cl.
*A61J 7/02* (2006.01)
*B65B 35/12* (2006.01)
*B65B 57/14* (2006.01)
*B65B 57/16* (2006.01)

(52) U.S. Cl.
CPC .............. *B65B 57/14* (2013.01); *B65B 57/16* (2013.01); *A61J 2200/70* (2013.01); *A61J 2205/10* (2013.01); *A61J 2205/20* (2013.01); *A61J 2205/30* (2013.01); *A61J 2205/60* (2013.01)

(58) Field of Classification Search
USPC .......... 53/131.4, 415, 473, 52, 135.3, 136.1, 53/155, 168, 171
See application file for complete search history.

(56) References Cited

U.S. PATENT DOCUMENTS

| | | | |
|---|---|---|---|
| 5,765,606 | A | 6/1998 | Takemasa et al. |
| 6,006,946 | A | 12/1999 | Williams et al. |
| 6,219,587 | B1 | 4/2001 | Ahlin et al. |
| 6,611,733 | B1 | 8/2003 | De La Huerga |
| 6,761,010 | B1 | 7/2004 | Gibson |
| 6,799,685 | B1 | 10/2004 | Yuyama et al. |
| 6,892,512 | B2 | 5/2005 | Rice et al. |
| 7,599,516 | B2 | 10/2009 | Limer et al. |
| 8,215,557 | B1 * | 7/2012 | Reno ................. G06K 7/10811 235/462.13 |
| 8,467,897 | B2 | 6/2013 | Holmes et al. |
| 8,511,478 | B2 | 8/2013 | Terzini |
| 8,682,047 | B2 | 3/2014 | Lang et al. |
| 8,861,816 | B2 | 10/2014 | Lang et al. |
| 8,943,779 | B2 | 2/2015 | Amano et al. |
| 9,449,148 | B2 | 9/2016 | Holmes |
| 9,727,701 | B2 | 8/2017 | Holmes et al. |
| 9,868,558 | B2 | 1/2018 | Holmes |
| RE46,910 | E | 6/2018 | Aylward et al. |
| 10,187,593 | B2 | 1/2019 | Holmes |
| 10,427,809 | B2 | 10/2019 | Holmes |
| 10,427,810 | B2 | 10/2019 | Holmes |
| 10,583,941 | B2 | 3/2020 | Holmes |
| 10,736,819 | B1 | 8/2020 | Nowosielski et al. |
| 11,410,764 | B1 | 8/2022 | Rosomoff et al. |
| 2002/0179619 | A1 | 12/2002 | Geltser et al. |
| 2005/0021173 | A1 | 1/2005 | Pinney et al. |
| 2005/0267356 | A1 | 12/2005 | Ramasubramanian et al. |
| 2007/0189597 | A1 * | 8/2007 | Limer ...................... A61J 7/02 382/128 |
| 2008/0300719 | A1 | 12/2008 | Duke |
| 2009/0012820 | A1 | 1/2009 | Bishop et al. |
| 2009/0076841 | A1 | 3/2009 | Baker et al. |
| 2010/0074496 | A1 | 3/2010 | Pao et al. |
| 2010/0277888 | A1 | 11/2010 | Yeh |
| 2011/0146835 | A1 | 6/2011 | Terzini |
| 2011/0184751 | A1 | 7/2011 | Holmes |
| 2011/0303692 | A1 | 12/2011 | Kim |
| 2012/0216485 | A1 | 8/2012 | Amano et al. |
| 2012/0239188 | A1 | 9/2012 | Sugimoto |
| 2013/0018503 | A1 | 1/2013 | Carson et al. |
| 2013/0020345 | A1 | 1/2013 | Kim |
| 2013/0218326 | A1 | 8/2013 | Chudy et al. |
| 2013/0284755 | A1 | 10/2013 | Yuyama et al. |
| 2015/0154750 | A1 | 6/2015 | Royaee |
| 2015/0190312 | A1 | 7/2015 | Yuyama et al. |
| 2016/0023787 | A1 | 1/2016 | Joplin |
| 2016/0114925 | A1 | 4/2016 | Yuyama et al. |
| 2016/0199260 | A1 | 7/2016 | Andersen, Sr. |
| 2017/0312178 | A1 | 11/2017 | Patel |
| 2017/0355476 | A1 | 12/2017 | Kim |
| 2017/0357775 | A1 | 12/2017 | Ekin |
| 2018/0012439 | A1 | 1/2018 | King et al. |
| 2018/0060525 | A1 | 3/2018 | Chen et al. |
| 2018/0125760 | A1 * | 5/2018 | Chessa ................... G01G 19/00 |
| 2018/0147120 | A1 | 5/2018 | Poirier et al. |
| 2018/0170591 | A1 | 6/2018 | Koike et al. |
| 2018/0263853 | A1 | 9/2018 | Yang |
| 2018/0333335 | A1 | 11/2018 | Carson et al. |
| 2019/0201292 | A1 | 7/2019 | Krezanoski |
| 2019/0307647 | A1 | 10/2019 | Greenspan et al. |
| 2020/0129379 | A1 | 4/2020 | Fukada |
| 2021/0052468 | A1 | 2/2021 | Whittier et al. |
| 2021/0086934 | A1 | 3/2021 | Burkett et al. |
| 2023/0011165 | A1 | 1/2023 | St Pierre et al. |
| 2023/0101967 | A1 | 3/2023 | Holmes |

FOREIGN PATENT DOCUMENTS

| | | | |
|---|---|---|---|
| CN | 1769138 | A | 5/2006 |
| CN | 101028292 | A | 9/2007 |
| CN | 104662579 | B | 12/2018 |
| JP | H0295373 | A | 4/1990 |
| JP | H07-299121 | A | 11/1995 |
| JP | H11-206855 | A | 8/1999 |
| JP | 2002-096802 | A | 4/2002 |
| JP | 2007-330411 | A | 12/2007 |
| JP | H11-114025 | A | 12/2014 |
| TW | 200930352 | A | 7/2009 |
| TW | I 608440 | B | 12/2017 |
| WO | 2009038378 | A2 | 3/2009 |
| WO | 2013105198 | A1 | 7/2013 |
| WO | 2014112221 | A1 | 7/2014 |
| WO | 2016194680 | A1 | 12/2016 |
| WO | 2017217366 | A1 | 12/2017 |
| WO | WO-2019195629 | A1 * | 10/2019 ............ A61J 7/0069 |

OTHER PUBLICATIONS

International Search Report with Written Opinion for related Application No. PCT/US2021/020529 dated Jul. 20, 2022 (17 Pages).

* cited by examiner

PHARMACEUTICAL COUNTING AND PACKAGING DEVICE

CROSS-REFERENCE TO RELATED APPLICATIONS

This application claims priority to U.S. Provisional Patent Application No. 62/984,143, filed Mar. 2, 2020, the entire contends of which are incorporated by reference herein.

FIELD OF THE INVENTION

The present invention relates to pharmaceutical packaging machines and, more particularly, a pharmaceutical counting machine for packaging pharmaceuticals.

SUMMARY

In one embodiment, the invention provides a method of filling a prescription including receiving, at an electronic processor of a pharmacy management system, a prescription to be filled by the pharmacy management system; generating, using the electronic processor, an information sheet for filling the prescription, the information sheet listing the medications needed to fill the prescription; retrieving one or more bulk storage containers containing medications to fill the prescription; packaging, using a pharmaceutical counting and packaging device, the medications from the one or more bulk storage containers into packages; and verifying, using the electronic processor, that the packages are correctly filled.

In another embodiment, the invention provides a method for packaging medications including scanning, using a scanner of a pharmaceutical counting and packaging device, a bulk storage container containing medications to fill a prescription; receiving a package in the packaging slot; verifying, using a verification system of the pharmaceutical counting and packaging device, that the package corresponds to the medication contained in the bulk storage container; counting, using a counter electronic processor of the pharmaceutical counting and packaging device, medications on a counting tray of the pharmaceutical counting and packaging device; determining, using the counter electronic processor, that the number of medications on the counting tray match the number of medications to fill the prescription; and filling the package with the counted medications when the number of medications on the counting tray match the number of medications to fill the prescription.

In yet another embodiment, the invention provides a pharmaceutical counting and packaging device including a counting tray, a counting camera system placed above the counting tray, a packaging slot provided below the counting tray to receive a package and including a verification system, a scanner, and a counter electronic processor electrically coupled to the scanner and the counting camera system. The counter electronic processor configured to scan, using the scanner, a bulk storage container containing medications to fill a prescription; verify, using the verification system, that the package corresponds to the medication contained in the bulk storage container; count medications on the counting tray; determine whether the number of medications on the counting tray match the number of medications to fill the prescription; prompt to add or remove medications from the counting tray when the number of medications on the counting tray does not match the number of medications to fill the prescription; and provide an indication that the number of medication on the counting tray matches the number of medications to fill the prescription when the number of medications on the counting tray matches the number of medications to fill the prescription.

In yet another embodiment, the invention provides a pharmaceutical counting device including a base portion and a counting tray provided on the base portion. The counting tray is configured to receive medications for counting by a camera system. The counting tray is tiltable about a first axis to empty the counted medications in the counting tray to a first package. The counting tray is tiltable about a second axis to empty the counted medications in the counting tray to a second package. The second package is of a different kind than the first package.

In yet another embodiment, the invention provides a pharmaceutical counting device including a base portion, a camera system provided above the base portion, and a counting tray provided on the base portion. The counting tray is configured to receive medications for counting by the camera system. The pharmaceutical counting device also includes a slot funnel provided in the base portion below the counting tray and a cartridge receiving slot in the base portion below the slot funnel. The cartridge receiving slot is configured to receive a cartridge of an automatic pharmaceutical packager. The counting tray is configured to be tilted about an axis to empty the counted medications into the cartridge received in the cartridge receiving slot.

In yet another embodiment, the invention provides a method for packaging medications using a pharmaceutical counting device including a counting tray configured to receive medications. The method includes receiving, at a pharmacy management system, a prescription to be filled and retrieving one or more bulk containers containing medications to fill the prescription. The method also includes receiving a plurality of medications from the one or more bulk containers on the counting tray and determining, using an electronic processor of the pharmaceutical counting device, that a correct number of medications to fill the prescription is received on the counting tray. The method further includes capturing, using a camera system of the pharmaceutical counting device, a first image of the correct number of medications on the counting tray and packaging, using the pharmaceutical counting device, the correct number of medications in a package. The method also includes capturing, using the camera system, a second image of the package including packaged medications within the package and generating, using the electronic processor, a transaction record corresponding to filling the prescription including the first image and the second image.

In yet another embodiment, the invention provides a pharmaceutical counting device including a base portion, a counting tray provided on the base portion and configured to receive medications for counting, a camera system including a camera positioned above the counting tray and configured to capture an image of contents of the counting tray, and an electronic processor coupled to the camera system. The electronic processor is configured to receive a prescription to be filled and determine, using the camera system, that a correct number of medications to fill the prescription is received on the counting tray. The electronic processor is also configured to capture, using the camera system, a first image of the correct number of medications on the counting tray and capture, using the camera system, a second image of a package including packaged medications within the package. The correct number of medications on the counting tray is packaged into the package. The electronic processor is further configured to generate a transaction record corresponding to filling the prescription including the first image and the second image.

In yet another embodiment, the invention provides a method for packaging medications using a pharmaceutical counting device including a counting tray configured to receive medications. The method includes receiving a plurality of medications on the counting tray and capturing, using a camera system of the pharmaceutical counting device, an image of the medications on the counting tray. The method also includes determining, using an electronic processor of the pharmaceutical counting device, whether a number of medications on the counting tray matches a desired number of medications provided on a prescription being filled by the pharmaceutical counting device based on the captured image and prompting, using a display device of the pharmaceutical counting device, to add or remove medications from the counting tray when the number of medications on the counting tray does not match the desired number of medications. The method further includes determining, using the electronic processor, whether a type of medication on the counting tray matches a desired type of medication provided on the prescription based on the captured image and prompting, using the display device, to remove medications from the counting tray when the type of medication on the counting tray does not match the desired type of medication. The method also includes providing, using the display device, an indication to proceed to packaging when the number of medications on the counting tray matches the desired number of medications and the type of medication on the counting tray matches the desired type of medication.

In yet another embodiment, the invention provides a pharmaceutical counting device including a base portion, a counting tray provided on the base portion and configured to receive medications for counting, a camera system including a camera positioned above the counting tray and configured to capture an image of contents of the counting tray, a display device, and an electronic processor coupled to the camera system and the display device. The electronic processor is configured to capture, using the camera system, an image of medications received on the counting tray. The electronic processor is also configured to determine whether a number of medications on the counting tray matches a desired number of medications provided on a prescription being filled by the pharmaceutical counting device based on the captured image and prompt, using the display device, to add or remove medications from the counting tray when the number of medications on the counting tray does not match the desired number of medications. The electronic processor is further configured to determine whether a type of medication on the counting tray matches a desired type of medication provided on the prescription based on the captured image and prompt, using the display device, to remove medications from the counting tray when the type of medication on the counting tray does not match the desired type of medication. The electronic processor is also configured to provide, using the display device, an indication to proceed to packaging when the number of medications on the counting tray matches the desired number of medications and the type of medication on the counting tray matches the desired type of medication.

In yet another embodiment, the invention provides a pharmaceutical counting device including a base portion, a camera system provided above the base portion, and a counting tray provided on the portion and configured to receive medications for counting by the camera system. The counting tray is configured to be tilted about an axis to empty the counted medications into a cartridge. The pharmaceutical counting device further includes a lock mechanism configured to lock the counting tray from being tilted to empty the medications into the cartridge and an electronic processor coupled to the camera system and the lock mechanism. The electronic processor is configured to activate the lock mechanism and capture, using the camera system, an image of the medications on the counting tray. The electronic processor is also configured to determine whether a number of medications on the counting tray matches a desired number of medications provided on a prescription being filled by the pharmaceutical counting device and determine whether a type of medication on the counting tray matches a desired type of medication provided on the prescription. The electronic processor is further configured to maintain the lock mechanism as activated when either the number of medications does not match the desired number of medications or the type of medication does not match the desired type of medication, or both. The electronic processor is also configured to deactivate the lock mechanism when the number of medications matches the desired number of medications and the type of medication matches the desired type of medication.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way but may also be configured in ways that are not listed.

Automatic packaging of pharmaceuticals for filling prescription results in lower error rate and time saving for pharmacies. However, the current automatic packagers available in the market may be too bulky or too expensive for low-volume pharmacies. Accordingly, there is a need for smaller and inexpensive counting machines and packagers for pharmacies.

Figure 1:
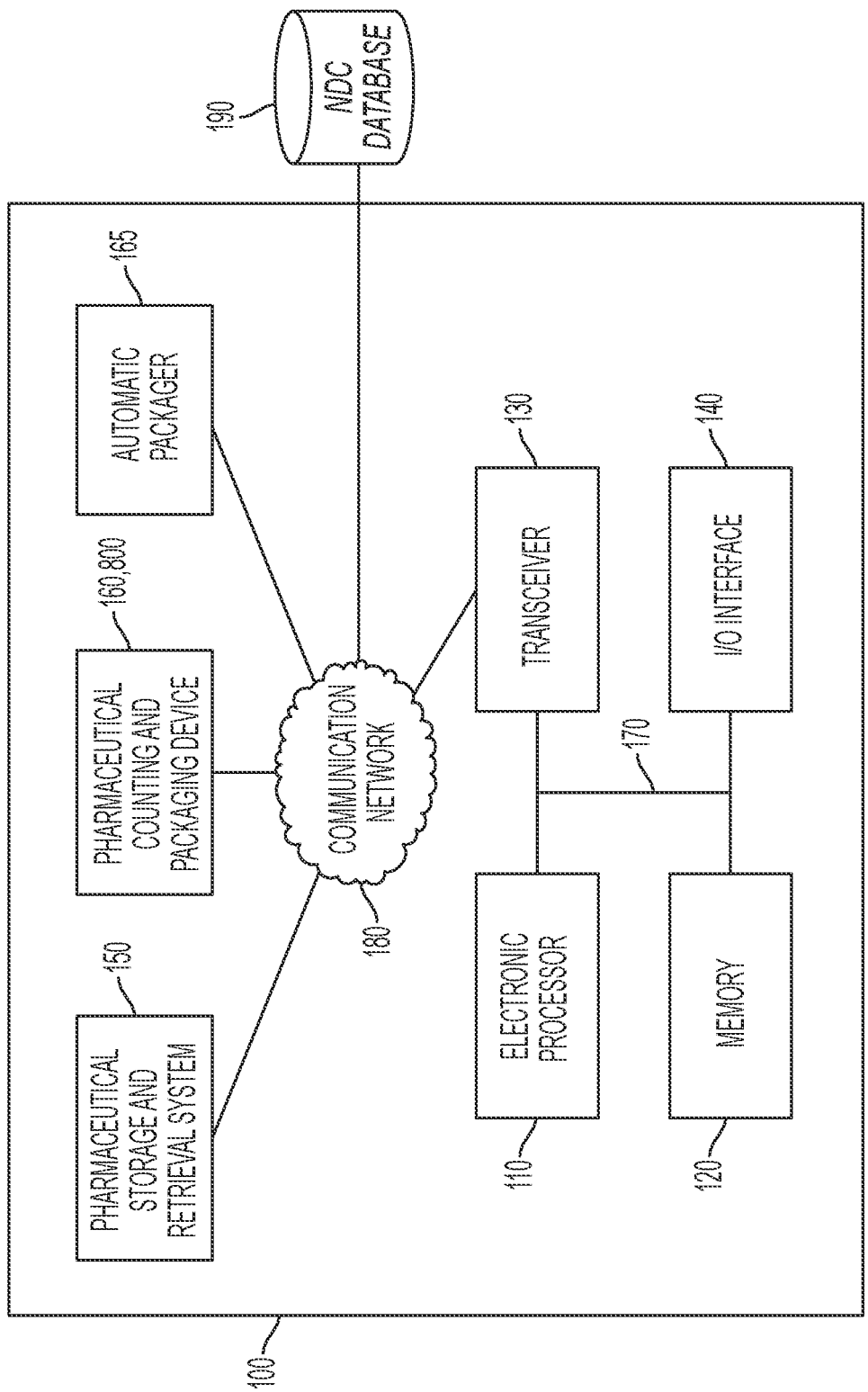
FIG. 1 is a schematic of a pharmacy management system in accordance with some embodiments.

FIG. 1 is a schematic illustration of a pharmacy management system 100 according to one example embodiment. The pharmacy management system 100 is a pharmacy automation system for use in retail pharmacies. The pharmacy management system 100 allows for automation of stocking the pharmacy, filling prescriptions, and inventory control performed in retail pharmacies. In the example illustrated in FIG. 1, the pharmacy management system 100 includes an electronic processor 110, a memory 120, a transceiver 130, an input/output interface 140, a pharmaceutical storage and retrieval system 150, a pharmaceutical counting and packaging device 160, and an automatic packager 165. The electronic processor 110, the memory 120, the transceiver 130, and the input/output interface 140 communicate over one or more control and/or data buses (e.g., a communication bus 170). FIG. 1 illustrates only one exemplary embodiment of the pharmacy management system 100. The pharmacy management system 100 may include more or fewer components and may perform functions other than those explicitly described herein. For example, in some embodiments, the pharmacy management system 100 may not include the pharmaceutical storage and retrieval system 150.

In some embodiments, the electronic processor 110 is implemented as a microprocessor with separate memory, such as the memory 120. In other embodiments, the electronic processor 110 may be implemented as a microcontroller (with memory 120 on the same chip). In other embodiments, the electronic processor 110 may be implemented using multiple processors. In addition, the electronic processor 110 may be implemented partially or entirely as, for example, a field-programmable gate array (FPGA), an application specific integrated circuit (ASIC), and the like, and the memory 120 may not be needed or be modified accordingly. In the example illustrated, the memory 120 includes non-transitory, computer-readable memory that stores instructions that are received and executed by the electronic processor 110 to carry out functionality of the pharmacy management system 100 described herein. The memory 120 may include, for example, a program storage area and a data storage area. The program storage area and the data storage area may include combinations of different types of memory, such as read-only memory and random-access memory.

The transceiver 130 enables wired or wireless communication from the pharmacy management system 100 to a communication network 180. In some embodiments, the transceiver 130 may include separate transmitting and receiving components, for example, a transmitter and a receiver. The pharmacy management system 100, through the communication network 180, may communicate with the pharmaceutical storage and retrieval system 150, the pharmaceutical counting and packaging device 160, and databases, for example, the National Drug Code (NDC) database 190.

The communication network 180 can be built according to any suitable networking technology or topology or combinations of technologies and topologies and can include multiple sub-networks. Connections between the devices and systems shown in FIG. 1 can be made through local area networks ("LANs"), wide area networks ("WANs"), public switched telephone networks ("PSTNs"), wireless networks, Intranets, the Internet, or any other suitable networks. In a hospital or medical care facility, for example, communication between the devices and systems shown in FIG. 1 can be made through any required communication protocol(s), including, for example, the Health Level Seven ("HL7") protocol or any other version of a required protocol. The HL7 protocol is a standard protocol which specifies the criteria for data exchange (including the required interface implementation) between two computer applications (sender and receiver), such that a universal standard is used by vendors, thereby facilitating the exchange of electronic data in health care environments. The HL7 protocol allows health care institutions to exchange key sets of data from different application systems. Specifically, the HL7 protocol can define the data to be exchanged, the timing of the interchange, and the communication of errors to the application. The formats are generally generic in nature and can be configured to meet the needs of the applications involved.

Figure 2:
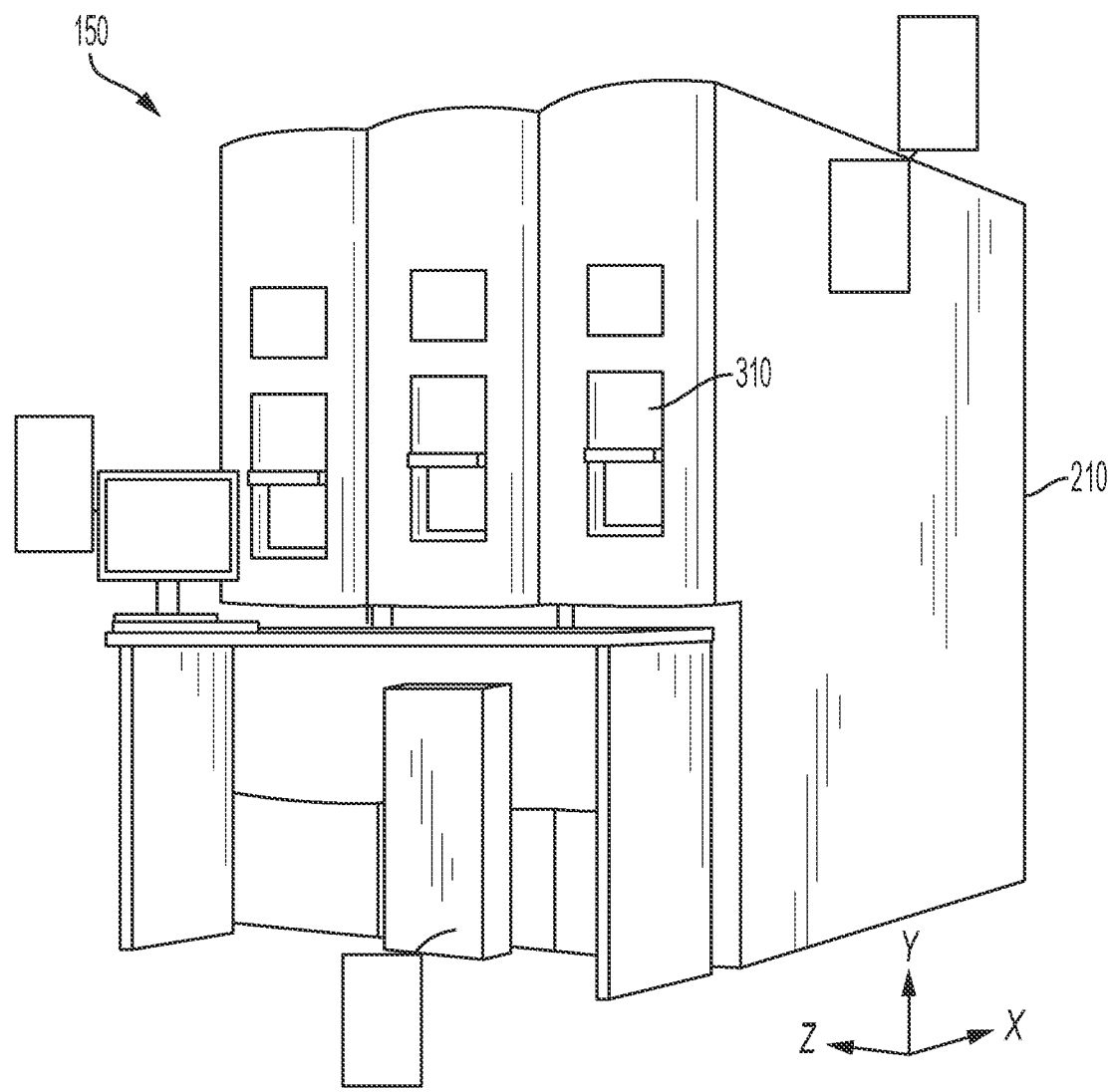
FIG. 2 is a perspective view of a pharmaceutical storage and retrieval system of the pharmacy management system of FIG. 1, the system having three storage and retrieval devices in accordance with some embodiments.

FIG. 2 illustrates a pharmaceutical storage and retrieval system 150 according to one example embodiment. The pharmaceutical storage and retrieval system 150 is a comprehensive workflow automation and high density robotic storage system for use in retail pharmacies. The system 150 seamlessly dispenses prescription containers and returns the containers to inventory without requiring operators to use a complicated software interface. As illustrated in FIG. 2, the pharmaceutical storage and retrieval system 150 includes one or more pharmaceutical storage and retrieval devices 210 and a computer or controller configured to control the operations and functionality of the pharmaceutical storage and retrieval device 210. Although the system 150 shown in FIG. 2 includes three pharmaceutical storage and retrieval devices 210, more or fewer devices 210 can be utilized in a particular pharmaceutical storage and retrieval system 150. Similar pharmaceutical storage and retrieval systems 150 are described and illustrated in U.S. Pat. No. 9,727,701, entitled "PHARMACEUTICAL STORAGE AND RETRIEVAL SYSTEM AND METHODS OF STORING AND RETRIEVING PHARMACEUTICALS," the entire contents of which are hereby incorporated by reference.

Figure 3:
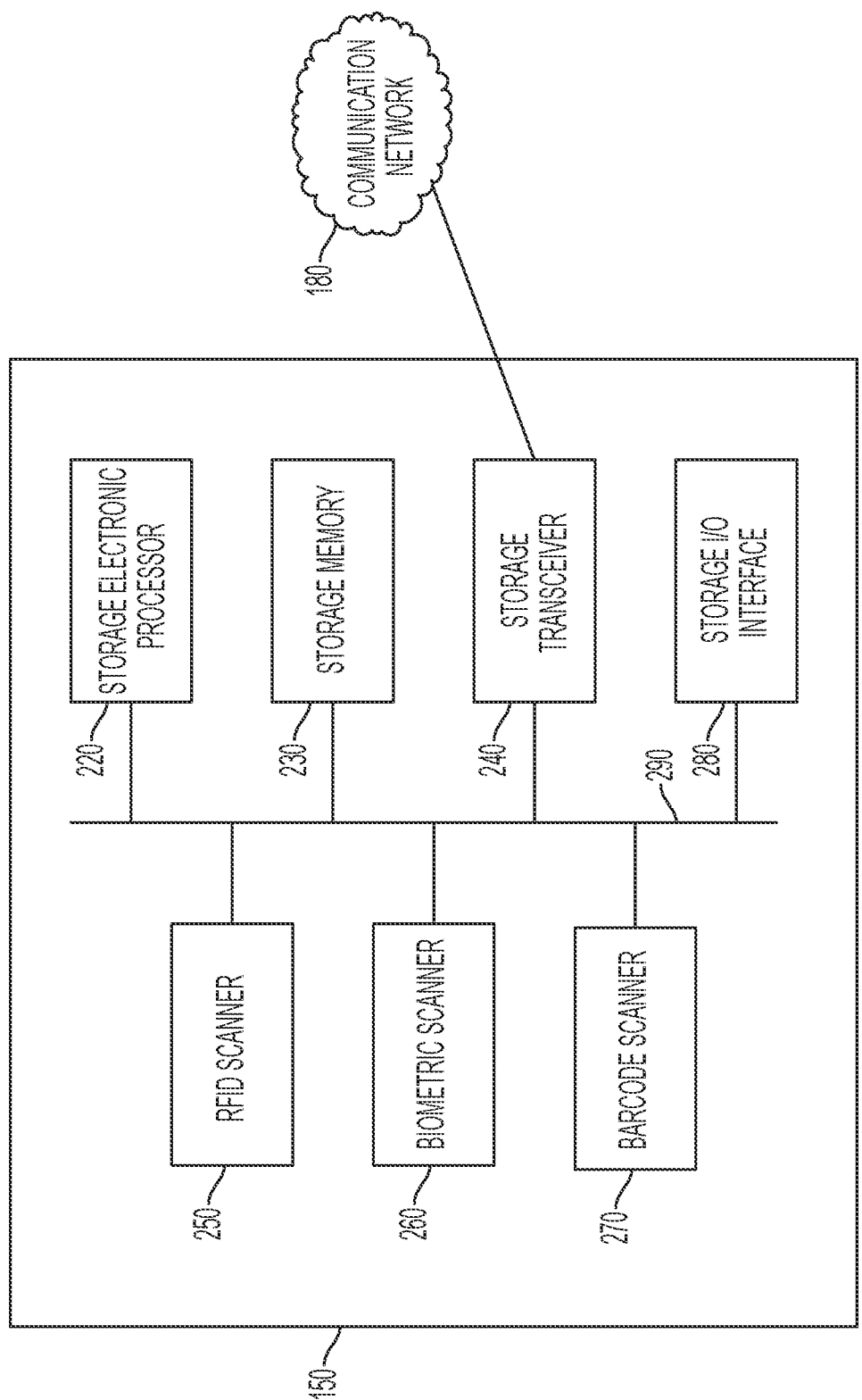
FIG. 3 is a schematic of the pharmaceutical storage and retrieval system illustrated in FIG. 2 in accordance with some embodiments.

FIG. 3 schematically illustrates the pharmaceutical storage and retrieval system 150 and its functionality within a pharmacy. In the example illustrated, the pharmaceutical storage and retrieval system 150 includes a storage electronic processor 220, a storage memory 230, a storage transceiver 240, an RFID scanner 250, a biometric scanner 260, a barcode scanner 270, and a storage input/output interface 280. The storage electronic processor 220, the storage memory 230, the storage transceiver 240, the RFID scanner 250, the biometric scanner 260, the barcode scanner 270, and the storage input/output interface 280 communicate over one or more control and/or data buses (e.g., a communication bus 290). FIG. 3 illustrates only one exemplary embodiment of the pharmaceutical storage and retrieval system 150. The pharmaceutical storage and retrieval system 150 may include more or fewer components and may perform functions other than those explicitly described herein.

The storage electronic processor 220 and the storage memory 230 may be implemented similar to the electronic processor 110 and the memory 120 as described above. The storage transceiver 240 enables communication from the pharmaceutical storage and retrieval system 150 to the communication network 180. In some embodiments, the storage transceiver 240 may include separate transmitting and receiving components, for example, a transmitter and a receiver. The pharmaceutical storage and retrieval system 150 through the communication network 180 may communicate with the pharmaceutical counting and packaging device 160 and databases, for example, the National Drug Code database 190.

The storage input/output interface 280 may include one or more input mechanisms (e.g., a touch screen, a keypad, a button, a knob, and the like), one or more output mechanisms (e.g., a display, a printer, a speaker, and the like), or a combination thereof. The storage input/output interface 280 receives input from the input devices actuated by a user, and provides output to the output devices with which a user interacts. In some embodiments, as an alternative or in addition to managing inputs and outputs through the storage input/output interface 280, the pharmaceutical storage and retrieval system 150 may receive user inputs, provide user outputs, or both by communicating with an external device, such as a console computer, over a wired or wireless connection.

Figure 4:
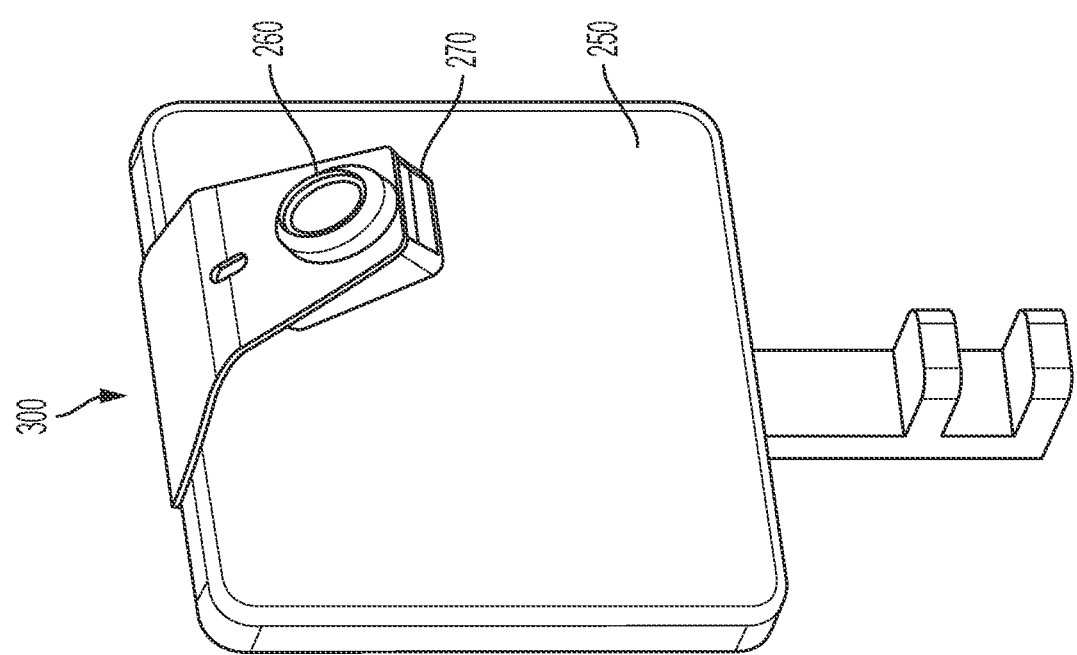
FIG. 4 is a perspective view of a user access assembly of the pharmaceutical storage and retrieval system of FIG. 2 in accordance with some embodiments.

As shown in FIG. 4, the pharmaceutical storage and retrieval system 150 also includes a user authorization system 300. The user authorization system 300 includes the RFID scanner 250, the biometric scanner 260, and the barcode scanner 270. The RFID scanner 250 is integral with the user authorization system 300. In alternate embodiments, the RFID scanner 250 can be separately located proximate the device 210. The biometric scanner 260 is used to identify an authorized user of the system 150 and can be, for example, a fingerprint scanner, an iris reader, a voice recognition scanner, a facial recognition scanner, or combinations thereof.

The barcode scanner 270 can be used to read barcodes such as the NDC on the containers or the labels on custom containers stored in the pharmaceutical storage and retrieval system 150. The barcode scanner 270 can also be used to scan unique barcode labels generated by the system 150 to identify individual containers of particular pharmaceuticals. In such embodiments, the system 150 generates a barcode that is uniquely assigned to each container that is stored in the device 210. As each container is first introduced into the device 210, a label bearing the system 150 generated barcode is affixed to the container. Thereafter, each time the container is "checked out" or "checked in" to the system 150, the system 150 cannot only identify the type of medication being "checked out" or "checked in," but can further track the specific container. Accordingly, such embodiments of the system 150 allow multiple containers of the same pharmaceutical or medication to be "checked out" of the system 150 at the same time. Because the system 150 can identify each specific container, the system 150 can associate each container with, for example, a specific operator or a specific prescription order to verify that the order was properly completed.

Referring back to FIG. 3, the storage electronic processor 220 may implement a fill prescription module for the pharmaceutical storage and retrieval system 150. In some embodiments, the fill prescription module is operable to retrieve a specific container to fill a customer's prescription from the system 150 using an automated process. In other embodiments, as noted above, the system 150 may be omitted. In such embodiments, a user may manually retrieve the specific container(s) from a location within a pharmacy, such as a closet or shelf. In scenarios where the system 150 is used to retrieve the specific container(s), when the pharmacy receives a prescription to fill, pharmacy personnel enter the information into the pharmacy management system 100, where the pharmacy printer generates an information sheet that includes a list of medications, customer information, and a barcode. The information sheet is taken to the scanner 270 where the barcode is read. At the same time, the user's RFID credential can be read to confirm authorization to the system 150 and the pharmaceuticals stored within. Based on the barcode, the fill prescription module instructs a gantry assembly of the pharmaceutical storage and retrieval device 210 to retrieve the container needed to fill the customer's prescription and identified on the information sheet. More specifically, the fill prescription module communicates with the storage memory 230 to obtain the particular location where the needed container of medication is stored within the device 210. The fill prescription module further communicates the particular location of the container to the gantry assembly so the gantry assembly knows where to go to retrieve the appropriate container. In the instance where a particular container is stored outside the device 210, an external storage location associated with the desired container can be communicated to the operator.

After identifying the particular location of the needed container, the gantry assembly retrieves the container and inserts it into a port 310 (FIG. 2) of the device 210. After the user's RFID credentials are verified, a front door opens to allow the user to remove the container from the port 310. The pharmacy management system 100 can also communicate the order information directly to the storage electronic processor 220 of system 150, which can direct the device 210 to begin retrieving and staging containers needed for the entered orders. Similar to the process described above, the user can take an information sheet generated by the pharmacy printer to the scanner 270 where the information sheet barcode and the user's RFID are read. If the system 150 recognizes a valid RFID credential and a barcode on the presented information sheet associated with a staged order, the port(s) 310 containing the pharmaceutical(s) needed to fill the order are opened. Accordingly, the system 150 can be configured to retrieve, but not allow access to the needed pharmaceuticals before the information sheet and RFID are scanned.

In scenarios where the system 150 is not present, when the pharmacy receives a prescription to fill, pharmacy personnel may still enter the information into the pharmacy management system 100 where the pharmacy printer generates in an information sheet. In this embodiment, however, the information sheet may not include a barcode to be scanned by a pharmaceutical storage and retrieval system 150. Instead, the information sheet may include a list of medications and customer information. The user may then manually retrieve bulk storage containers containing the desired medications from a storage location (e.g., a closet, a cabinet, a shelf, etc.). As such, the information sheet may also include location information (e.g., aisle and shelf information) for each medication. Alternatively, the user may directly retrieve the desired bulk storage containers without first entering the information into the pharmacy management system 100 and generating the information sheet.

Figure 5:
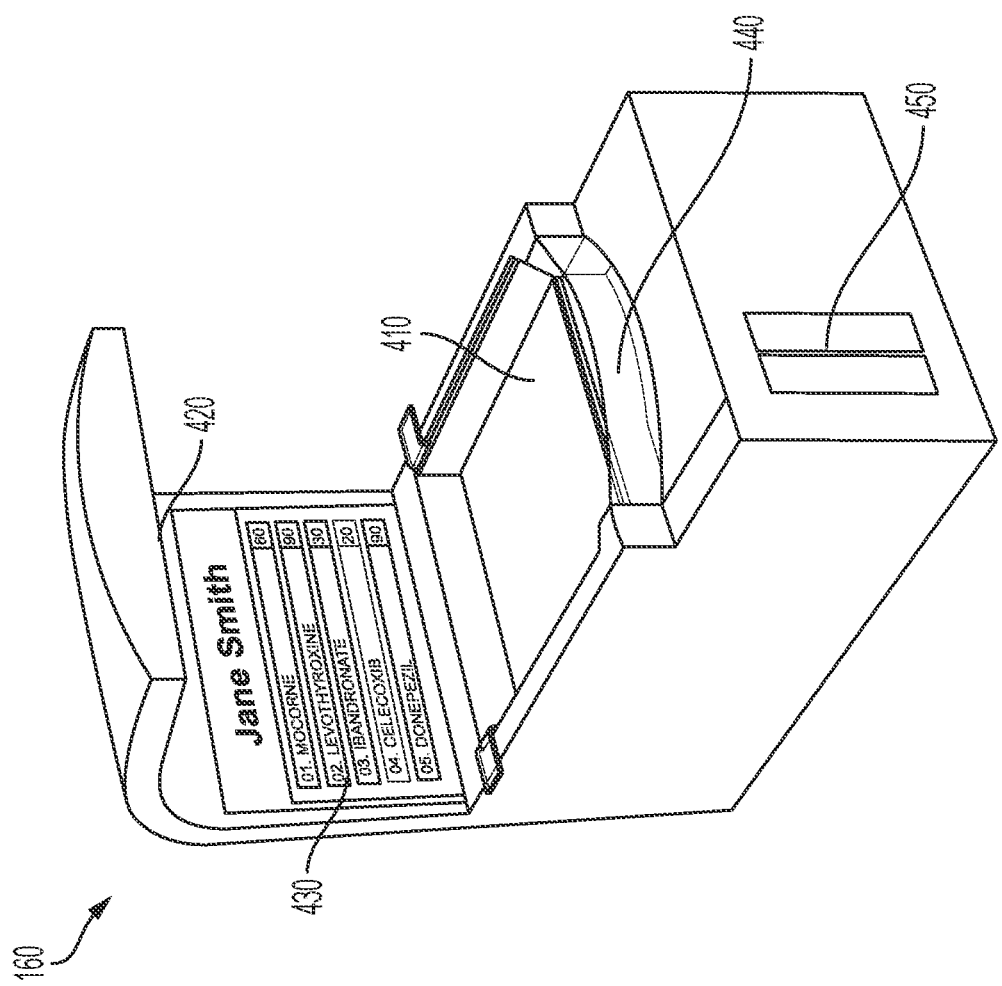
FIG. 5 is a perspective view of a pharmaceutical counting and packaging device of the pharmacy management system of FIG. 1 in accordance with some embodiments.

FIG. 5 illustrates the pharmaceutical counting and packaging device 160 according to one example embodiment. The pharmaceutical counting and packaging device 160 is a medication counting and packaging device for use in retail pharmacies that detects and counts a number of medications that are placed on the pharmaceutical counting and packaging device 160. The pharmaceutical counting and packaging device 160 displays the count and shares the count with other systems within the pharmacy. As illustrated in FIG. 5, the pharmaceutical counting and packaging device 160 includes a counting tray 410, a counting camera system 420, a display 430, a funnel 440, and a packaging slot 450.

The counting camera system 420 may include a barcode scanner 540 (see FIG. 7) and an imaging system for counting the medications on the counting tray 410. The barcode scanner 540 is used to scan a barcode on a label of a bulk container retrieved from the device 210 or other location within the pharmacy and may be implemented similar to the barcode scanner 270. In some embodiments, the pharmaceutical counting and packaging device 160 may include other types of scanners, such as a scanner for recognizing a Q-code on a bottle or a camera for recognizing an image of or on the bottle. In further embodiments, the barcode scanner may be omitted and a user may directly enter information regarding a bottle into the pharmaceutical counting and packaging device 160 (e.g., a serial number of the bottle via a keypad). The contents of the bulk container may then be placed on the counting tray 410 for counting by the pharmaceutical counting and packaging device 160. The counting tray 410 may be replaceable for cleaning and to inhibit cross-contamination between different types of medications. The counting tray 410 is pivotably attached to a housing of the pharmaceutical counting and packaging device 160 such that a user can lift the counting tray 410 to direct the medications on the counting tray 410 into the funnel 440 without having to touch the medications. The funnel 440 is shaped to guide the medications from the counting tray 410 into the packaging slot 450. The packaging slot 450 is provided below the funnel 440 to receive a package for packaging the medications counted on the counting tray 410.

The counting tray 410 may be transparent or translucent such that a lighting system 550 (see FIG. 7) underneath the counting tray 410 can illuminate the contents of the counting tray 410. Once illuminated, the counting camera system 420 may capture an image of the contents of the counting tray 410 to commence counting. The display 430 may be used to display the scanned barcode information and to display the count of the medications placed on the counting tray 410. Based on the displayed information, a pharmacist or technician may add or remove medications from the counting tray 410 until the correct amount of medications is placed on the counting tray 410. When the correct amount of medications is placed on the counting tray 410, the user may transfer the contents of the counting tray 410 to the packaging slot 450. The user may transfer the contents of the counting tray 410 by lifting the counting tray 410 to guide the medications into the packaging slot 450 through the funnel 440. In some embodiments, a lockout mechanism may be provided for the counting tray 410. The lockout mechanism of the counting tray 410 prevents the counting tray 410 from being lifted when an incorrect amount of medications are placed on the counting tray 410 (that is, when the lockout mechanism is activated). The lockout mechanism of the counting tray 410 may be unlocked (that is, deactivated) when the correct amount of medications are placed on the counting tray 410, such that the pharmacist may lift the counting tray 410 to transfer the medications to the packaging slot 450.

Figure 6:
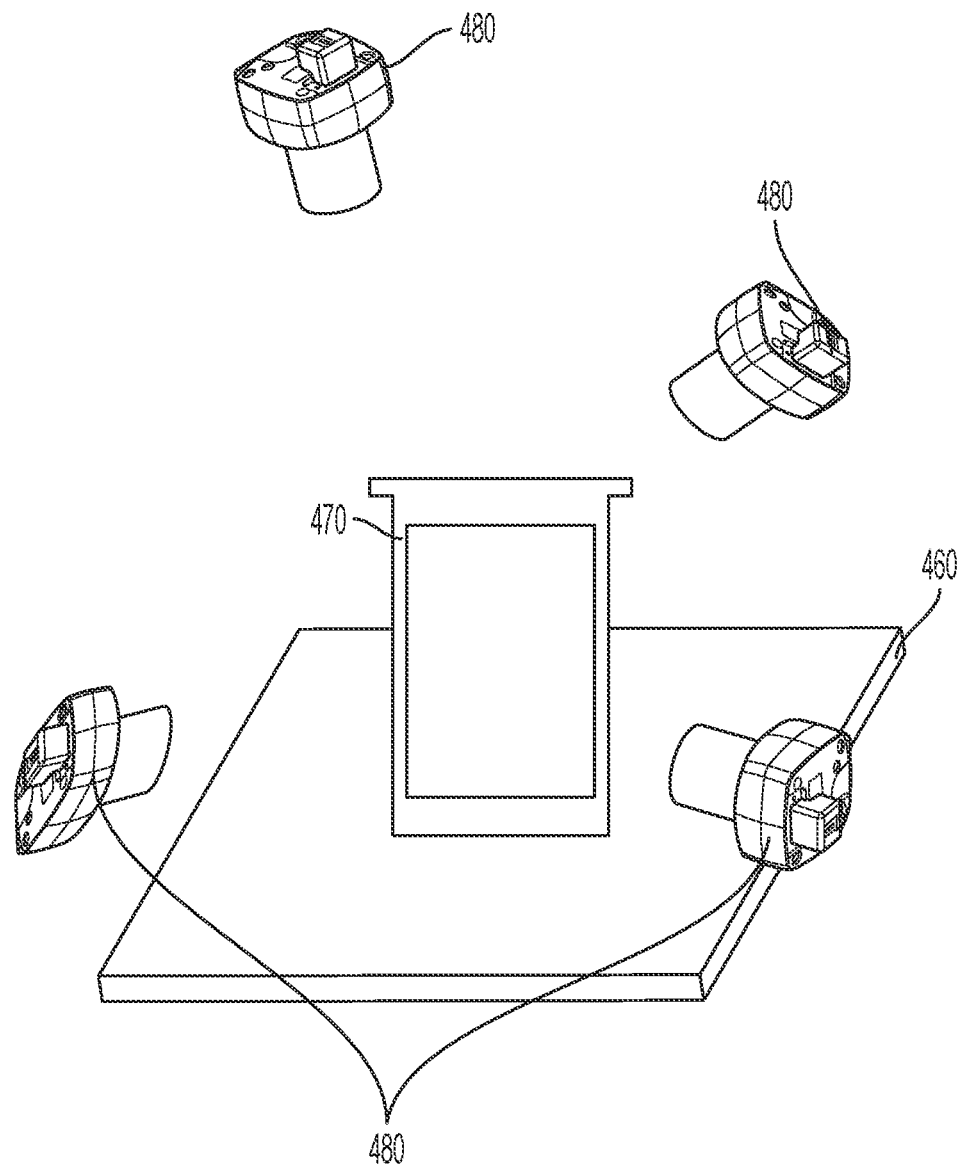
FIG. 6 is a perspective view of a packaging slot of the pharmaceutical counting and packaging device of FIG. 5 in accordance with some embodiments.

FIG. 6 illustrates the packaging slot 450 according to one example embodiment. The packaging slot 450 facilitates packaging of the counted medications into packages and verification of packaged medication. As illustrated in FIG. 6, the packaging slot 450 includes a platform 460, a package 470, and a verification system 480.

The platform 460 provides a base for receiving the package 470. In the example illustrated, the package 470 is a pill vial. In other embodiments, the package 470 may be another suitable container. The platform 460 may include additional features to help in the placement of the package 470 on the platform 460. For example, the platform 460 may include raised features to guide the placement of the package 470 in the packaging slot 450. In the example illustrated in FIG. 6, the verification system 480 is a verification camera system 480. The verification camera system 480 includes one or more cameras placed in the packaging slot 450 to capture the exterior and/or interior of the package 470. In the example illustrated, the packaging slot 450 includes three cameras placed 120 degrees apart to capture the exterior of the package 470. The cameras may be placed at the same height of the package 470 (for example, a vial) to capture a barcode or label placed on the package 470. The packaging slot 450 may also include a camera placed above the package to capture contents of the package 470. The lighting system 550 (see FIG. 7) may be used to illuminate the package 470 and the contents of the package 470 during image capture by the verification camera system 480. In some embodiments, the verification camera system 480 is used to verify that a correct packaging vial is placed on the platform 460. The verification camera system 480 programmatically unpeels the label to present the label information in a readable format. The counter electronic processor 510 then verifies the information from the unpeeled label to determine whether the correct packaging vial is placed on the platform 460.

In some embodiments, rather than multiple cameras, the verification camera system 480 may include one or more cameras provided in combination with one or more mirrors placed such that the one or more cameras can capture the entire label of the packaging vial. In some embodiments, the pharmaceutical counting and packaging device 160 may include a mechanism to rotate the platform 460. The one or more cameras may be used to capture multiple images of the packaging vial while the platform 460 is rotated to present several views of the packaging vial to the one or more cameras. In some embodiments, rather than moving the platform 460, the one or more cameras and/or the mirrors may be rotated around the platform 460 to capture several views of the packaging vial.

In some embodiments, the verification system 480 may include other verification components rather than a verification camera system 480. For example, the verification system 480 includes an RFID detector that detects an RFID chip integrated into the label of the packaging vial. The verification system 480 may include a barcode or QR code scanner to scan a 1-dimensional or 2-dimensional barcode provided on the packaging vial. In other embodiments, the packaging vial may be verified at other locations. For example, the packaging vial is verified at a pharmacist's computer, using the counting camera system 120, or at a separate verification machine or camera system. In some embodiments, a label application component may be provided in the pharmaceutical counting and packaging device 160 to apply a correct label to the packaging vial while the packaging vial is in the packaging slot 450 before or after the packaging vial is filled.

Figure 7:
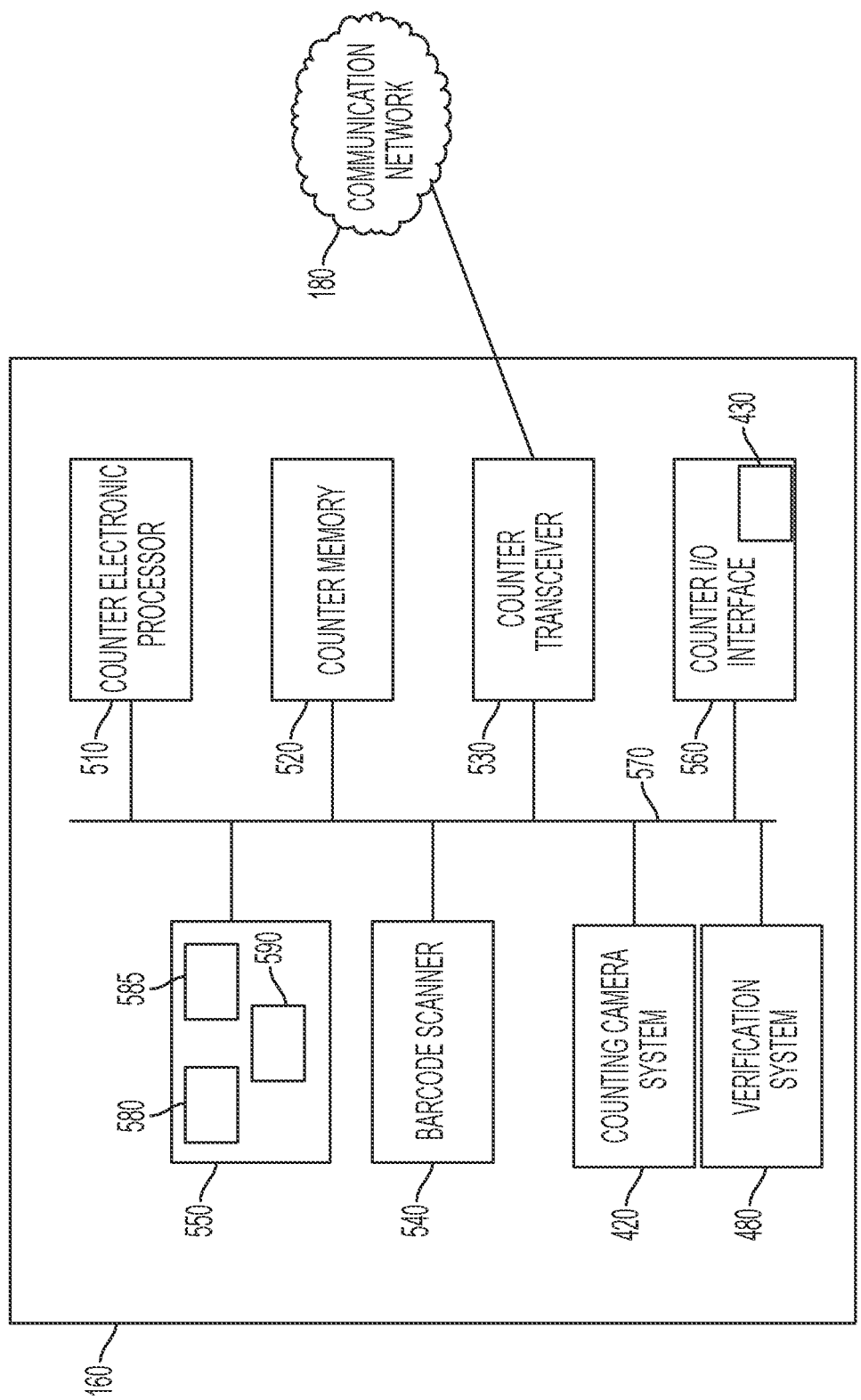
FIG. 7 is a schematic of the pharmaceutical counting and packaging device of FIG. 5 in accordance with some embodiments.

FIG. 7 schematically illustrates the pharmaceutical counting and packaging device 160 and its functionality within a pharmacy. In the example illustrated, the pharmaceutical counting and packaging device 160 includes a counter electronic processor 510, a counter memory 520, a counter transceiver 530, the barcode scanner 540, the counting camera system 420, the display 430, the verification system 480, the lighting system 550, and a counter input/output interface 560. The counter electronic processor 510, the counter memory 520, the counter transceiver 530, the barcode scanner 540, the counting camera system 420, the display 430, the verification camera system 480, the lighting system 550, and the counter input/output interface 560 communicate over one or more control and/or data buses (e.g., a communication bus 570). FIGS. 5-7 illustrate only one exemplary embodiment of the pharmaceutical counting and packaging device 160. The pharmaceutical counting and packaging device 160 may include more or fewer components and may perform functions other than those explicitly described herein.

The counter electronic processor 510 and the counter memory 520 may be implemented similar to the storage electronic processor 220 and the storage memory 230 as described above. Although certain drawings illustrate hardware and software located within particular devices, these depictions are for illustrative purposes only. In some embodiments, the illustrated components may be combined or divided into separate software, firmware, and/or hardware. For example, instead of being located within and performed by a single electronic processor, logic and processing may be distributed among multiple electronic processors. Regardless of how they are combined or divided, hardware and software components may be located on the same computing device or may be distributed among different computing devices connected by one or more networks or other suitable communication links. Here, for example, the counter electronic processor 510 may not be provided or may be provided in a different location and the functionality described below may be performed by the other electronic processors 110 and 210. In some embodiments, one or more of the electronic processors 110, 210, 510 are provided in a cloud computer cluster arrangement, one or more of which may be executing none, all, or a portion of the applications of the pharmaceutical counting and packaging device 160, 800 provided below, sequentially or in parallel across the one or more electronic processors 110, 210, 510. The one or more electronic processors 110, 210, 510 may be geographically co-located or may be separated by inches, meters, kilometers, or miles, and interconnected via electronic and/or optical interconnects. One or more proxy servers or load balancing server may control which one or more electronic processors 110, 210, 510 perform any part or all applications described herein.

The counter transceiver 530 enables communication from the pharmaceutical counting and packaging device 160 to the communication network 180. In some embodiments, the counter transceiver 530 may include separate transmitting and receiving components, for example, a transmitter and a receiver. The pharmaceutical counting and packaging device 160 through the communication network 180 may communicate with the pharmaceutical storage and retrieval system 150 and databases, for example, the National Drug Code database 190.

The counter input/output interface 560 may include one or more input mechanisms (e.g., a touch screen, a keypad, a button, a knob, and the like), one or more output mechanisms (e.g., a display, a printer, a speaker, and the like), or a combination thereof. The counter input/output interface 560 receives input from the input devices actuated by a user, and provides output to the output devices with which a user interacts. In some embodiments, as an alternative or in addition to managing inputs and outputs through the counter input/output interface 560, the pharmaceutical counting and packaging device 160 may receive user inputs, provide user outputs, or both by communicating with an external device, such as a console computer, over a wired or wireless connection.

The lighting system 550 includes a first light source 580, a second light source 585, and a third light source 590. The first light source 580 is positioned under the counting tray 410. In some embodiments, the first light source 580 is an infrared (IR) or near infrared (NIR) spectrum light. In other embodiments, the first light source 580 is a visible spectrum light. The first light source 580 shines light through the counting tray 410 toward the counting camera system 420 to illuminate the contents of the counting tray 410. When the first light source 580 illuminates the counting tray 410, the medications on the counting tray 410 form shadows against a white background of the first light source 580 or the counting tray 410. The counting camera system 420 captures an image of the shadows cast by the medications on the counting tray 410. The image may be a still image of the medications at a specific instance of time, or may be a live image that is continuously transmitted to the display 430. In some embodiments, the first light source 580 is provided in concentric circles under the counting tray 410. For example, the first light source 580 includes three concentric rings of light provided below the counting tray 410. The concentric rings arrangement distributes the light evenly across the counting tray 410. Specifically, the intensity of the three concentric rings of light may be adjusted to balance the light from the camera's perspective. By adjusting the intensity, the contrast and color intensity may be maintained uniform across the counting tray 410 when viewed from the camera. In other embodiments, an attenuator may be used with the first light source 580 or the camera system 420 to maintain uniformity in the light across the counting tray 410.

The second light source 585 (e.g., a visible spectrum light) is positioned on the same side of the counting tray 410 as the counting camera system 420 to shine light on the counting tray 410 and illuminate the contents of the counting tray 410. When the second light source 585 illuminates the counting tray 410, the counting camera system 420 captures a visible light image of the medications, showing the color, shape, contour, surface finish, etc. of the medications. The image may be a still image of the medications at a specific instance of time, or may be a live image that is continuously transmitted to the display 430. The counting camera system 420 communicates with the counter electronic processor 510 and the counter memory 520 to store the images and/or transmit the images to the display 430. The third light source 590 (e.g., a visible spectrum light) is positioned in the packaging slot 450 to illuminate the package 470 and the contents of the package 470. When the third light source 590 illuminates the package 470 and contents, the verification camera system 480 captures visible light images of the label placed on the package 470 and the contents of the package 470. The images captured by the verification camera system 480 may be transmitted to the display 430 for review by the pharmacist.

Figure 8:
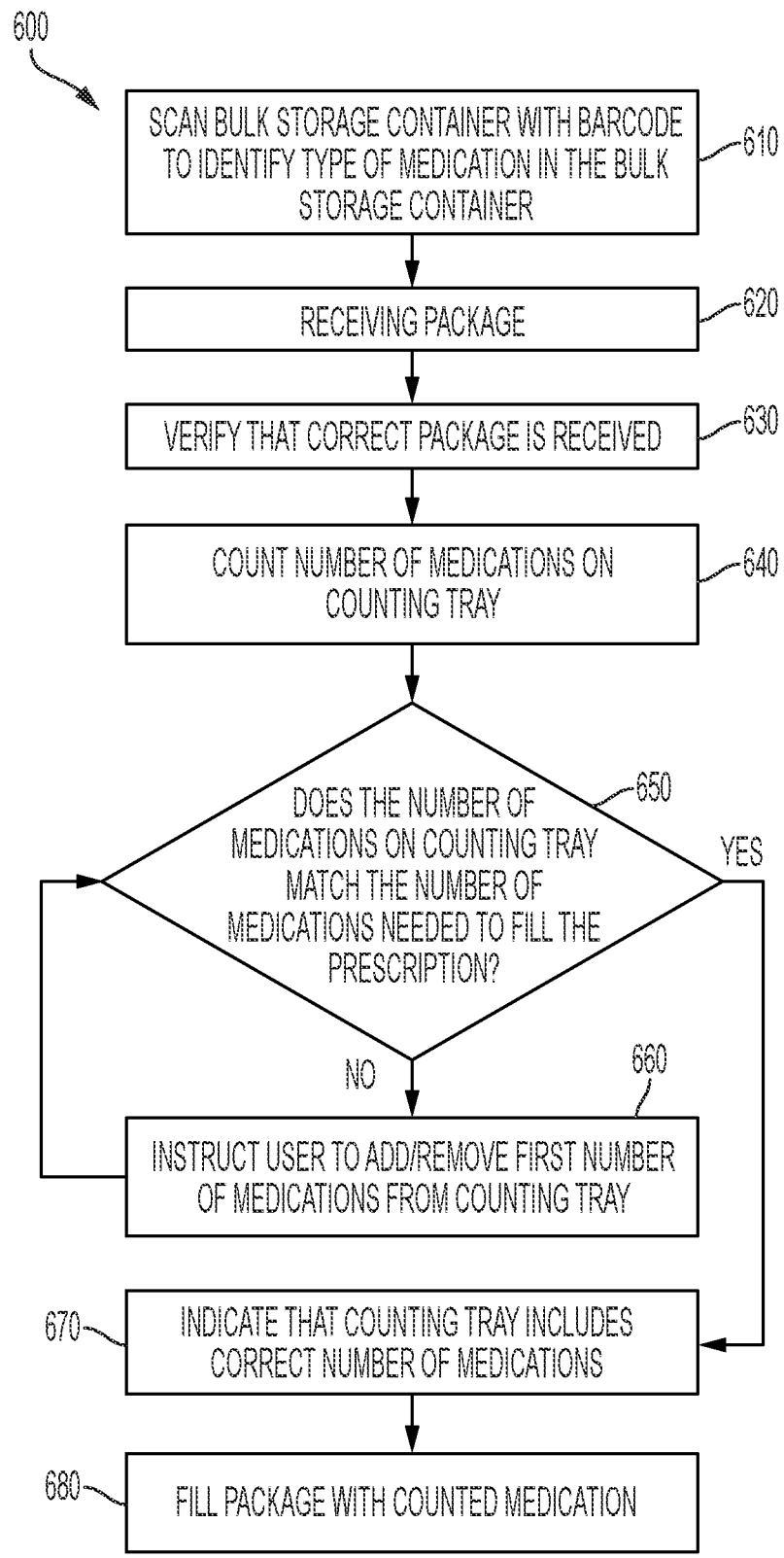
FIG. 8 is a flowchart of a method of packaging medications for filling a prescription in accordance with some embodiments.

FIG. 8 depicts a method 600 of packaging medications for filling a prescription. Although the method 600 includes specific blocks, all the blocks need not be performed or performed in the order presented. When the pharmacist receives a prescription from a customer, the pharmacy management system 100 generates an information sheet including a list of all the medications required to fill the prescription. The pharmacist uses the information sheet to retrieve bulk containers including the medications in the information sheet. For example, the pharmacist retrieves the bulk container from the pharmaceutical storage and retrieval system 150 or from storage shelves in the pharmacy.

At block 610, the method 600 includes scanning, using the counter electronic processor 510 with the barcode scanner 540, a bulk storage container with a barcode to identify the type of medication in the bulk storage container. Once the pharmacist retrieves the bulk storage containers, the pharmacist scans the bulk storage containers at the pharmaceutical counting and packaging device 160. The barcode scanner 540 scans the barcode on the bulk storage containers and provides the identification information read from the barcode to the counter electronic processor 510. The counter electronic processor 510 retrieves information pertaining to the medication within the bulk storage container using the identification information. For example, the counter electronic processor 510 communicates with the NDC database 190 to determine the type, the weight, the size, the color, etc. of the medication within the bulk storage container. Scanning the bulk storage containers at the pharmaceutical counting and packaging device 160 also verifies that the correct bulk storage containers were retrieved.

At block 620, the method 600 includes receiving a package 470. The package 470 is, for example, a vial, a container, or the like in which the prescribed medications are packaged and provided to the customer. In some embodiments, the package 470 is received in the packaging slot 450. For example, the pharmacist may place the package in the packaging slot 450 through the doors of the packaging slot 450. In some embodiments, the pharmaceutical counting and packaging device 160 may indicate to the user on the display 430 to place the package 470 in the packaging slot 450. In some embodiments, the doors of the packaging slot 450 may be locked until an authorized user logs into the pharmaceutical counting and packaging device 160. Additionally or alternatively, the doors may be locked until a valid prescription order is entered into the pharmaceutical counting and packaging device 160. In some embodiments, the package 470 may be received at other locations. For example, the package 470 may be received at a front packaging funnel (not shown) of the pharmaceutical counting and packaging device 160.

At block 630, the method 600 includes verifying that the correct package 470 is received. The verification camera system 480 or other verification system as described above is used to verify that a correct label has been applied to the package 470. The counter electronic processor 510 captures images of the label of the package 470 using the verification camera system 480. For example, the verification camera system 480 includes three cameras placed 120 degrees apart in the packaging slot 450 to capture the label placed around a vial or container placed in the packaging slot 450. The counter electronic processor 510 activates the third light source 590 and the cameras to capture the images and combine the images to produce a single label image. The counter electronic processor 510 may use known image processing techniques to process the single label image to determine the information printed on the label placed on the package 470. The counter electronic processor 510 may then verify the information on the label with the information from the prescription to determine whether the correct package 470, for example, with the correct label is received in the packaging slot 450. The counter electronic processor 510 may also display the image or images of the label and the information on the label on the display 430 for verification by the pharmacist. Certain kinds of medications may require special packaging material. The counter electronic processor 510 may also use the images captured using the verification camera system 480 to determine whether the kind of package 470 used corresponds to the medications being filled in the package 470.

In some embodiments, when the counter electronic processor 510 determines that the correct package 470 is received in the packaging slot 450, the counter electronic processor 510 may lock the doors of the packaging slot 450. When the counter electronic processor 510 determines that the label on the package 470 is incorrect, corresponds to a different medication, is the wrong kind of package 470, or the like, the pharmaceutical counting and packaging device 160 may indicate to the user on the display 430 to replace the package 470 with a corrected package 470.

At block 640, the method 600 includes counting, using the counter electronic processor 510 with the counting camera system 420, the number of medications on the counting tray 410 of the pharmaceutical counting and packaging device 160. After scanning a bulk storage container, the pharmacist pours medications from the bulk storage container onto the counting tray 410. The counter electronic processor 510 activates the first light source 580 to illuminate the counting tray 410 and captures an image of the counting tray 410 using the counting camera system 420 to determine the number of medications on the counting tray 410. In some embodiments, the first light source 580 may always be turned on when the pharmaceutical counting and packaging device 160 is turned on. As described above, the first light source 580 is an IR or a NIR light source that cast shadows of the medications against a white background. The counter electronic processor 510 processes the image captured by the counting camera system 420 using known image processing systems to determine the number of medications on the counting tray 410. Particularly, the counter electronic processor 510 analyzes the shadows cast by the medications to determine the number of medications on the counting tray 410. In some embodiments, the pharmaceutical counting and packaging device 160 continuously captures the image of the counting tray 410 at regular time intervals (e.g., every 0.5 seconds) to update the count of the medications.

The counter electronic processor 510 also captures the visible light images of the medications on the counting tray 410. The counter electronic processor 510 processes the IR images and the visible light images to isolate portions of the images corresponding to individual medications. The counter electronic processor 510 determines an expected medication type to be counted using the pharmaceutical counting and packaging device based on the scanned bulk storage container. The counter electronic processor 510 compares the isolated images of the medications on the counting tray with the images of expected medication types pre-stored in the counter memory 520 or received from the NDC database 190. When the medications on the counting tray 410 do not match the expected medications type, the counter electronic processor 510 prompts the user to remove medications from the counting tray 410. For example, the counter electronic processor 510 provides an indication on the display 430 that the medications on the counting tray do not match the expected medications.

At block 650, the method 600 determines whether the number of medications on the counting tray 410 matches the number of medications needed to fill the prescription. The pharmaceutical counting and packaging device 160 may receive the prescription information or the label sheet information from the pharmacy management system 100. The pharmaceutical counting and packaging device 160 determines the number of medications needed to fill the prescription from the prescription information or the label sheet information. Particularly, the pharmacist may scan the information sheet generated by the pharmacy management system 100 using the barcode scanner 540. The pharmacy management system 100 sends the information included on the information sheet to the pharmaceutical counting and packaging device 160. The electronic processor 110 of the pharmacy management system 100 communicates with the pharmaceutical counting and packaging device 160 using the transceiver 130 and the communication network 180 to provide the information on the information sheet to the counter electronic processor 510. The counter electronic processor 510 retrieves the information received from the pharmacy management system 100 based on scanning the bar code on the information sheet. The pharmaceutical counting and packaging device 160 compares the number of medications on the counting tray 410 to the number of medications needed to fill the prescription.

When the number of medications on the counting tray 410 does not match the number of medications needed to fill the prescription, the pharmaceutical counting and packaging device 160 instructs the user to add/remove a first number of medications from the counting tray 410, at block 660. The pharmaceutical counting and packaging device 160 determines the difference between the number of medications on the counting tray 410 and the number of medications needed to fill the prescription and indicates to the user (e.g., using the display 430) to add or remove the first number of medications corresponding to the difference between the number of medications on the counting tray 410 and the number of medications needed to fill the prescription. For example, if 30 medications are needed to fill the prescription, but 32 medications are poured onto the counting tray 410, the pharmaceutical counting and packaging device 160 instructs the user to remove 2 pills and return the pills to the bulk container. Conversely, if 30 medications are needed to fill the prescription, but 28 medications are poured onto the counting tray 410, the pharmaceutical counting and packaging device 160 instructs the user to add 2 pills to the counting tray 410 from the bulk container. As described above, the method 600 then returns to block 650 to continuously determine the number of medications on the counting tray 410.

When the number of medications on the counting tray 410 matches the number of medications needed to fill the prescription, the pharmaceutical counting and packaging device 160 indicates that the counting tray 410 includes the correct number of medications, at block 670. The pharmaceutical counting and packaging device 160 may also process the images captured to identify whether any medications are broken or whether the counting tray 410 includes any debris. The pharmaceutical counting and packaging device 160 instructs the pharmacist to remove the broken medications or debris from the counting tray 410.

At block 680, the method 600 includes filling the package 470 with the counted medication. The counter electronic processor 510 deactivates the lockout mechanism of the counting tray 410 such that the user may lift the counting tray 410 to fill the medications in the package 470 received in the packaging slot 450. The pharmacist then empties the medications on the counting tray 410 into the package 470. The method 600 is repeated for each medication in the prescription to fill different packages 470. This allows the pharmacist to fill the exact number of medications needed to fill the prescription into the packages 470 and does not need to dump excess medications from the packages 470 back into the bulk storage container after packaging.

In some embodiments the packaging slot 450 may not include a discrete door or doors. For example, the packaging slot 450 includes a drawer-like mechanism which is pulled in and out automatically similar to a consumer Compact Disc (CD) drive, where when the drawer opens, the package can then be placed in a cupholder-like location on the drawer. The drawer could then be pushed into the slot by the operator and retained by a latch, or automatically drawn in by a powered mechanism. When the drawer is closed, access to the packaging slot 450 is blocked by the end of the drawer, which functions as a door. When filling and verification of the package are complete, the drawer latch could be released by an internal mechanism or solenoid and open under spring power like the drawer of a cash register, allowing the operator to remove the package. Alternatively, the drawer could be propelled open via a motor. Verification cameras and/or mirrors may be imbedded in the slot drawer as well as placed inside the pharmaceutical counting and packaging device 160.

In other embodiments, the pharmaceutical counting and packaging device 160 may include additional and/or reserve packaging slots 450. The user may place multiple packages in the packaging slots 450 that form a queue to be filled by the pharmaceutical counting and packaging device 160. The pharmaceutical counting and packaging device 160 may include multiple packaging queues for different sizes of the pharmaceuticals. The pharmaceutical counting and packaging device 160 may automatically apply a label to the packages after each job is completed or may include a printer to print a label that is then applied by the user to the filled packages. In some embodiments, the pharmaceutical counting and packaging device 160 may include a mechanism to automatically apply a cap or lid to the package being filled by the pharmaceutical counting and packaging device 160.

In addition to counting the number of medications, the pharmaceutical counting and packaging device 160 may also be used to determine one or more characteristics of the medications. For example, the pharmaceutical counting and packaging device 160 may be used to determine the color, shape, and/or dimensions of the medications. The NDC information received from the NDC database 190 generally includes information regarding the color and size of the medications within set ranges. The pharmacy management system 100 communicates the color and size information with the pharmaceutical counting and packaging device 160 for verification during packaging. However, there may be variations in the shade of the color (e.g., shade of blue) and size during manufacturing. For example, when manufacturing the medications, the medications do not always come out with the same color quality. A medication may be identified as blue in the database, but the shade of blue may be slightly different in the actual medication. Similarly, a medication may be identified in the database as having a diameter of 2 to 3 millimeters, and the actual size of the medication may be anywhere within that range.

As described above, the pharmaceutical counting and packaging device 160 is used to capture an image of the medications in the IR/NIR, and visible light spectrum using the counting camera system 420 to determine one or more characteristics of the medications. For example, the counter electronic processor 510 activates the second light source 585 and captures an image of the counting tray 410 including the medications using the counting camera system 420. The counter electronic processor 510 processes the image captured by the counting camera system 420 using known image processing techniques to determine the actual color (e.g., a particular shade of color) of the medications. Similarly, the counter electronic processor 510 processes the image captured by the counting camera system 420 to determine the actual size (e.g., a measured size) of the medications. The counter electronic processor 510 can determine if the actual color and actual size are within the ranges of expected color and expected size provided by the NDC database 190. The pharmaceutical counting and packaging device 160 correlates the color information and the size information with the identification information of the medication determined after scanning the barcode of the bulk storage container. The pharmaceutical counting and packaging device 160 may store and transmit the color information and the size information for each medication in the prescription to the pharmacy management system 100. In some embodiments, the pharmaceutical counting and packaging device 160 may only measure one characteristic (e.g., color, shape, or size) associated with each medication. In further embodiments, the pharmaceutical counting and packaging device 160 may also or alternatively determine and compare other characteristics of the medications, such as weight (e.g., via a scale integrated into the counting tray 410), shape, and the like.

In some embodiments, rather than using the NDC database 190, the pharmaceutical counting and packaging device 160 may be trained for one or more types of medications. For example, when a medication type is first received by the pharmaceutical counting and packaging device 160, the pharmaceutical counting and packaging device 160 may capture several images of the medication to determine the characteristics of the medication. These characteristics are then later used for verification that a correct medication is provided on the counting tray 410. The captured images may be stored on the pharmaceutical counting and packaging device 160. In some embodiments, the captured images are uploaded to a master database that is remote from the pharmaceutical counting and packaging device 160. The master database may receive captured images from several pharmaceutical counting and packaging devices 160 located in different retail locations. The captured images are used for mathematical comparison between a current pharmaceutical on the counting tray 410 and the captured images to determine whether the correct pharmaceutical matching the prescription data is placed on the counting tray 410. In some embodiments, if the pharmaceutical counting and packaging device 160 does not include captured images for comparison, the pharmaceutical counting and packaging device 160 may check whether these images are available on the master database. For example, the captured images may be uploaded by a different pharmaceutical counting and packaging device 160 at a different location. The pharmaceutical counting and packaging device 160 at the current location then downloads the captured images and uses the captured images for verifying the pharmaceutical on the counting tray 410. In some embodiments, the information from the NDC database 190 may be used as a starting point, which is then refined by the characteristics determined from the image captures by the pharmaceutical counting and packaging device 160. In some embodiments, the user may be prompted to verify that a correct medication is being used by displaying characteristics provided by the NDC database 190.

Figure 9:
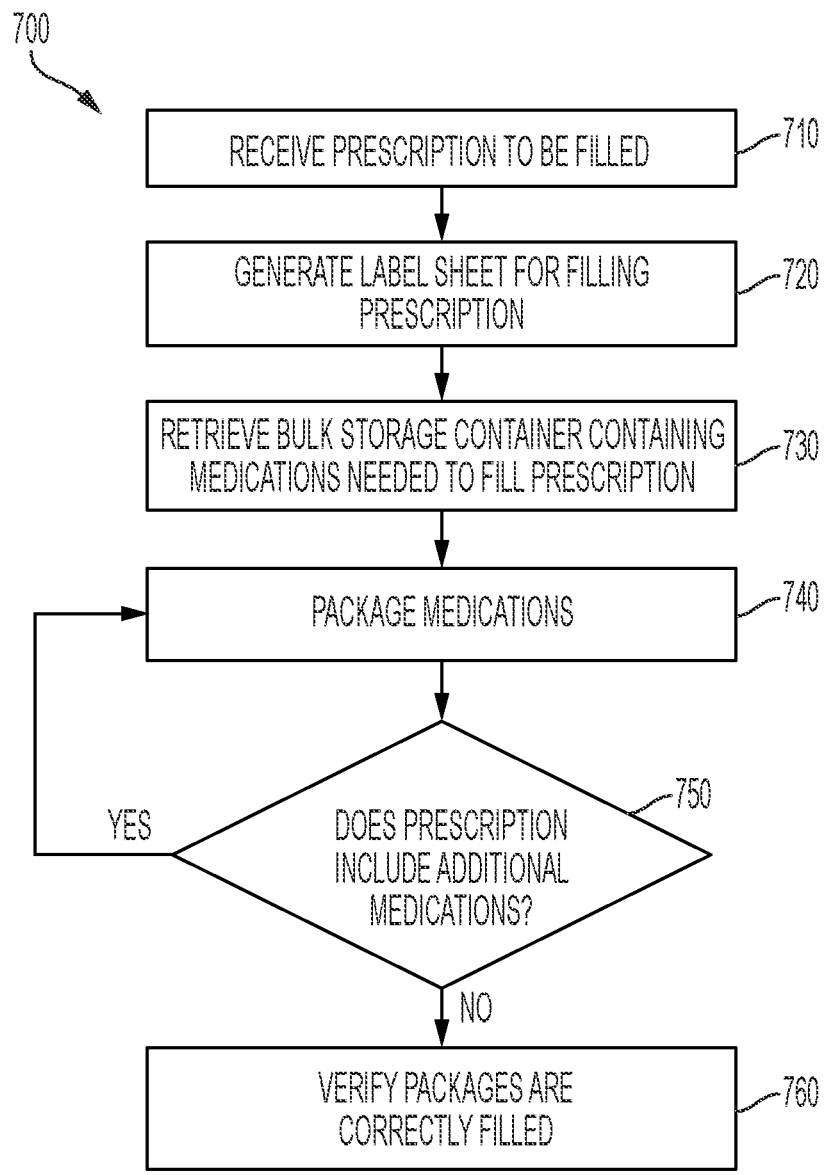
FIG. 9 is a flowchart of a method of filling a prescription in accordance with some embodiments.

FIG. 9 depicts a method 700 for filling a prescription in a pharmacy. Although the method 700 includes specific blocks, all the blocks need not be performed or performed in the order presented. The pharmacy is an automated pharmacy including the pharmaceutical storage and retrieval system 150 and the pharmaceutical counting and packaging device 160 as described above. As noted above, the pharmaceutical storage and retrieval system 150 may be omitted. The method 700 leverages the automated nature of the pharmacy to verify the correct type and/or number of pharmaceuticals are loaded into each package as part of filling the prescription. The package may take any form, for example, a pouch package, a blister card package, a pill vial, and the like. In particular, the method 700 involves providing a verification system for a pharmacist to verify filling the prescription from when the prescription is received until the pharmaceuticals are loaded and sealed in a package to create a chain of custody for the pharmaceuticals. The chain of custody may be stored as an electronic file in the memory 120 of the pharmacy management system 100 or a remote computer or server.

At block 710, the method 700 includes receiving, at the electronic processor 110, a prescription to be filled by the pharmacy management system 100. In one embodiment, the prescription may be received electronically through the communication network 180 from a healthcare facility. In other embodiments, the prescription may be received by scanning a paper prescription presented by a customer or by manually entering the contents of the prescription presented by the customer into the pharmacy management system 100.

At block 720, the method 700 includes generating, with the electronic processor 110, an information sheet for filling the prescription. Generating the information sheet may include the pharmacy management system 100 electronically generating a list of medications (for example, including identifying information of the medications) provided in the prescription and transmitting the information sheet to the pharmaceutical storage and retrieval system 150 and/or the pharmaceutical counting and packaging device 160. In other embodiments, the pharmacy management system 100 prints the information sheet using a pharmacy printer. The pharmacist may then physically carry the information sheet to be scanned by the pharmaceutical storage and retrieval system 150 and/or the pharmaceutical counting and packaging device 160.

At block 730, the method 700 includes retrieving bulk storage containers containing the medication needed to fill the prescription. As described above, the pharmaceutical storage and retrieval system 150 retrieves the containers including the medications for the prescription to be picked up by the pharmacist in response to receiving or scanning the information sheet at the pharmaceutical storage and retrieval system 150. In other embodiments, the pharmacist may manually retrieve the containers including the medications from storage shelves of the pharmacy based on the information sheet.

At block 740, the method 700 includes packaging, using the pharmaceutical counting and packaging device 160, the medications in a package 470. A method for packaging the medications is described above with respect to FIG. 8. At block 750, the method 700 includes determining whether the prescription includes additional medications to be processed. The pharmaceutical counting and packaging device 160 counts and packages each type of medication needed to fill the prescription. When the pharmacy management system 100 determines that there are additional medications to be processed, the method 700 returns to block 740 to process the next medication in the prescription. When the pharmacy management system 100 determines that all the medications in the prescription are processed and filled into the packages 470, the method proceeds to block 760.

At block 760, the method 700 includes verifying that the packages 470 are correctly filled. As described above, the pharmaceutical counting and packaging device 160 provides the one or more characteristics of the medications to the pharmacy management system 100. The pharmaceutical counting and packaging device 160 may also provide identifying information along with an image (e.g., from the captured images) and a final count (e.g., before the counting tray 410 is emptied) of the medications to the pharmacy management system 100. The pharmacy management system 100 receives the information from the pharmaceutical counting and packaging device 160 and displays the information on a display of the pharmacy management system 100 for verification by the pharmacist. In some embodiments, the pharmaceutical counting and packaging device 160 displays the contents of the counting tray 410 as captured by the pharmaceutical counting and packaging device 160. Each of the medications on the counting tray 410 are then numbered on the display to show the count. For example, when 10 medications are desired to be counted, the pharmaceutical counting and packaging device 160 labels each of the medications on the counting tray 410 with a number between 1 and 10 to show that the counting tray 410 includes the correct number of verifications. This image is then stored in the counter memory 520 along with the transaction data corresponding to the current package for later verification if needed.

The pharmacist may be located in the same building or room as the pharmaceutical counting and packaging device 160 or may be located remotely. In one example, the pharmacy management system 100 compares the image of the medication received from the pharmaceutical counting and packaging device 160 to an image available on, for example, the NDC database 190. The pharmacy management system 100 may also display the image received from the pharmaceutical counting and packaging device 160 side-by-side with the image available on the NDC database 190 for verification by the pharmacist. The pharmacy management system 100 may indicate whether the correct medications were filled in the packages 470 to a user. The indication may include providing a colored border around an image of each medication. This provides an opportunity for the pharmacist to identify any errors prior to the medications being packaged.

In some embodiments, the pharmaceutical counting and packaging device 160 may capture images of the contents of the package 470. The counter electronic processor 510 activates the verification camera system 480, for example, a camera placed above the package 470, to capture an image of the contents of the filled package 470. The counter electronic processor 510 may transmit the image of the contents of the filled package 470 to the pharmacy management system 100 for verification. The counter electronic processor 510 may also display the image of the contents of the filled package 470 on the display 430 for verification by the pharmacist. The image of the contents of the filled package 470 may be displayed simultaneously with the other images.

Figure 10:
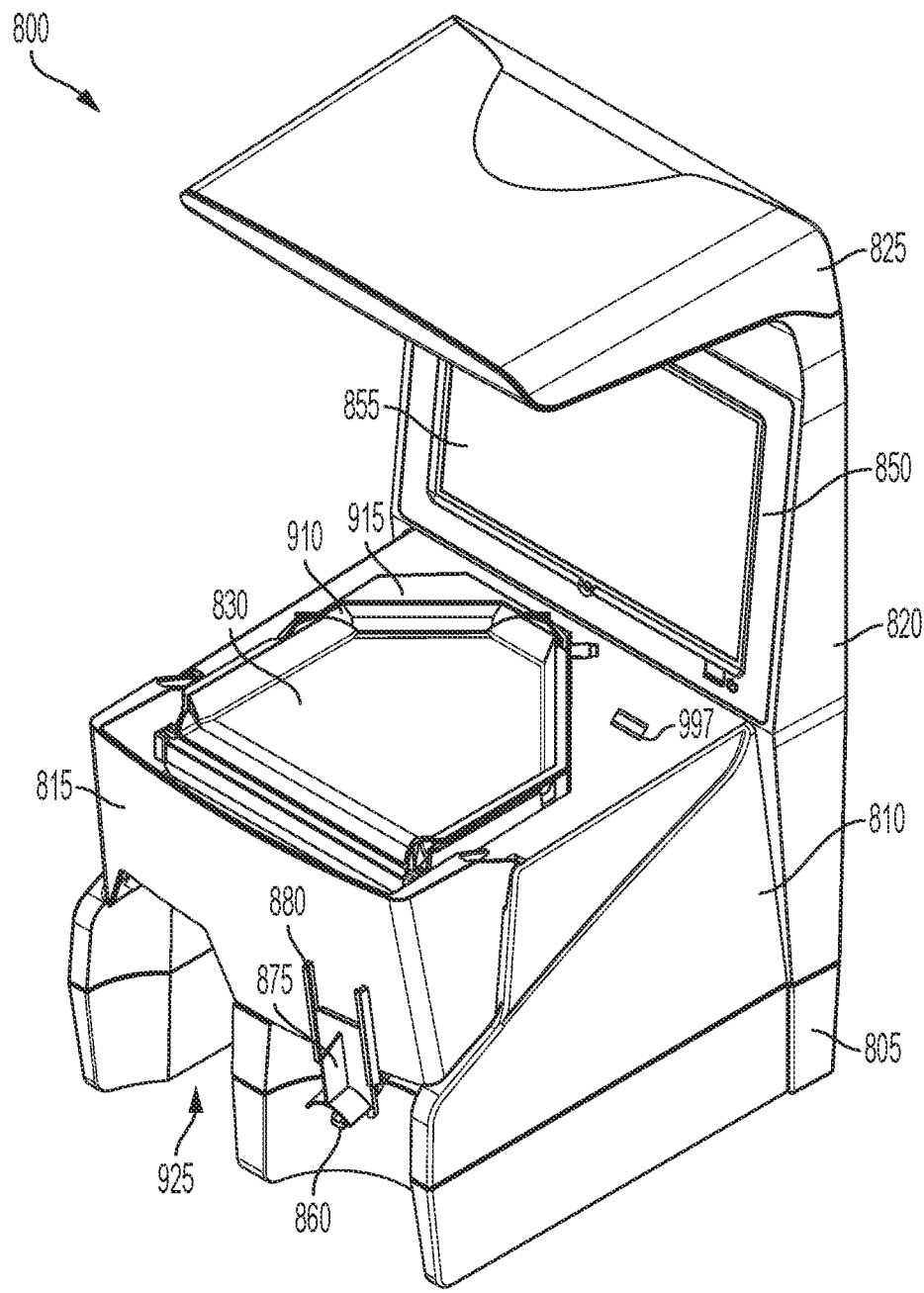
FIG. 10 is a perspective view of a pharmaceutical counting device of the pharmacy management system of FIG. 1 in accordance with some embodiments.
Figure 11:
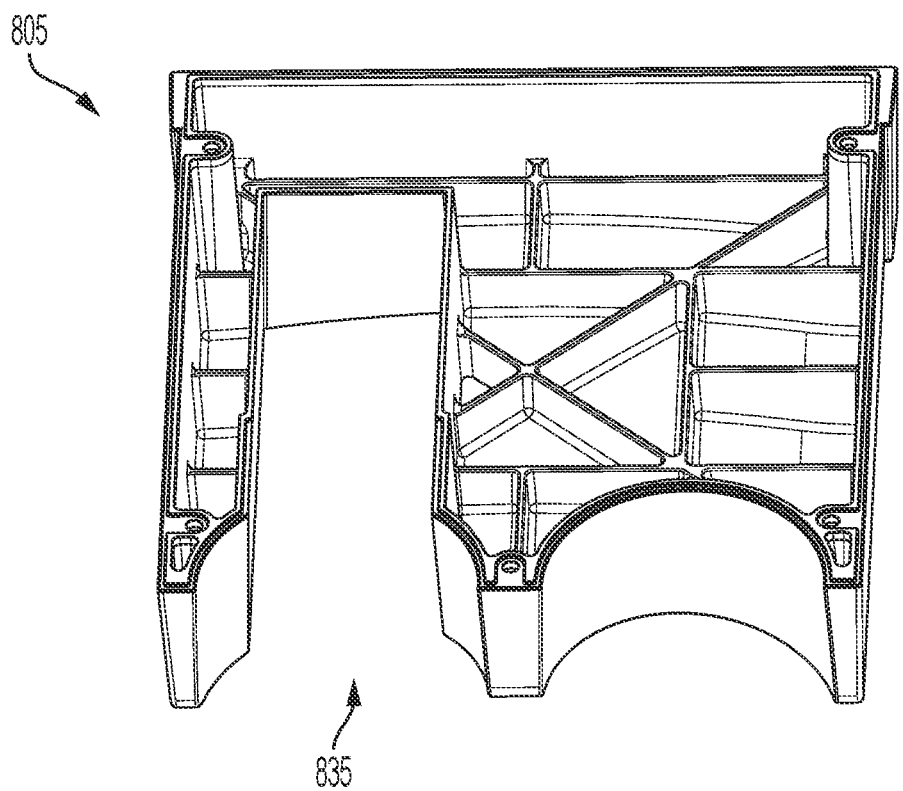
FIG. 11 is a perspective view of a removable base of the pharmaceutical counting device of FIG. 10 in accordance with some embodiments.

FIG. 10 illustrates one example of a pharmaceutical counting device 800. The pharmaceutical counting device 800 includes a base 805, a base portion 810, a front panel 815, a back panel 820, a top panel 825, and a tray 830. In some embodiments, the base 805 may be removable from the rest of the pharmaceutical counting device 800, and may be referred to as a removable base. The removable base 805 is removably attached to the base portion 810 using, for example, a ship lap connection, a slide-on connection, fasteners, or the like. The removable base 805 is provided to alter the dimensions of the pharmaceutical counting device 800 to fit different applications of the pharmaceutical counting device 800. The removable base 805 may be used with the pharmaceutical counting device 800 when, for example, the pharmaceutical counting device 800 is used in conjunction with the pharmaceutical storage and retrieval 150 and/or with the automatic packager 165. The pharmaceutical counting device 800 may be used without the removable base 805 when, for example, the pharmaceutical counting device 800 is used as a stand-alone device. Referring to FIG. 11, the removable base 805 includes a slot portion 835 that receives a cartridge 985 (shown in FIG. 20). In some embodiments, the removable base 805 includes fastener openings to receive fasteners that attach the removable base 805 to the pharmaceutical counting device 800.

Figure 12:
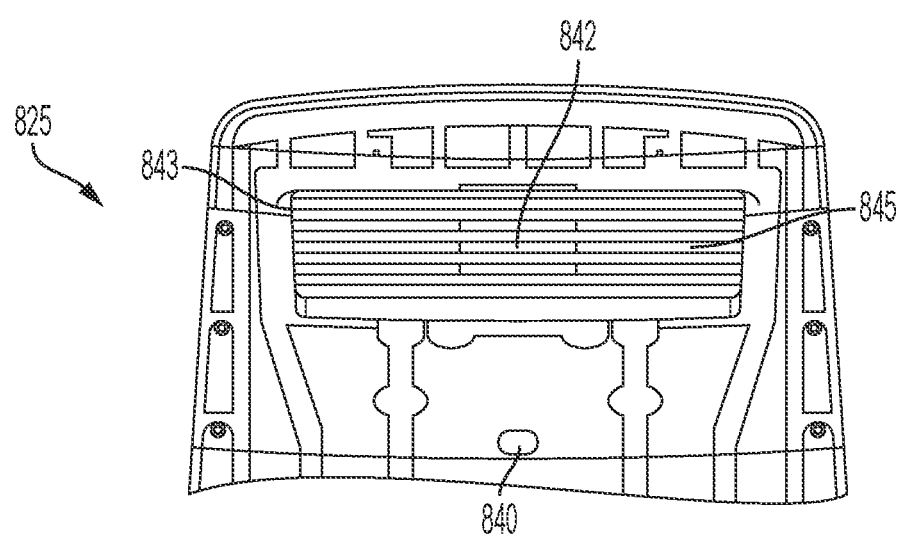
FIG. 12 is a plan view of a top panel of the pharmaceutical counting device of FIG. 10 in accordance with some embodiments.

Referring to FIG. 12, the top panel 825 includes a bar code sensor 840, a top camera 842, and a light panel 845. The bar code sensor 840 is used to read a bar codes printed on bulk storage containers and packaging vials. The light panel 845 is provided towards the front of the top panel 825 and includes light sources in the visible spectrum that illuminate the contents of the tray 830. The light panel 845 may also include a diffuser to diffuse the light from the light source such that the light is evenly distributed over the tray 830. The top camera 842 is provided in the middle of the light panel 845 and captures images of the contents of the tray 830. In some embodiments, one or more louvers 843 is provided below the light panel 845. The one or more louvers 843 direct the light onto the tray 830 and reduce or inhibit the light from interfering with a pharmacist's or technician's (for example, user's) observation of the tray 830.

Referring to FIG. 10, the back panel 820 is fixed to a back of the base portion 810 and may be made of a single piece or may include one or more pieces attached together. The illustrated back panel 820 includes a device slot 850 to receive a display device 855. For example, the back panel 820 may include a bottom piece to support the base portion 810 and a top piece to support the display device 855. The display device 855 is, for example, a graphics display coupled to a computing device of the pharmaceutical counting device 800. In some embodiments, the display device 855 is a tablet computer that is removably placed in the device slot 850. The display device 855 may include a camera (for example, a display device camera) to capture images in front of the display device above the tray 830. In some embodiments, the display device 855 also includes a camera to capture images of, for example, the bulk storage containers, the packaging vials, and the like. The camera of the display device 855 can also be used as a biometric scanner to verify the identity of a person operating the pharmaceutical counting device 800. In some embodiments, the camera of the display device 855 is used to capture an image of the packaging label on the packaging vials. Specifically, once the medications on the tray 830 are emptied into a packaging vial, the packaging vial with a label affixed is placed on the tray 830. The camera on the display device 855 is then used to capture the image of label. The label image is stored in the counter memory 520 as part of a transaction record for later verification if needed. The back panel 820 may additionally include vents or a fan to dissipate heat generated by the display device 855. The fan may be electronically controlled based on detecting temperature of the display device 855, an operating load on the display device 855, and/or the like.

Figure 13:
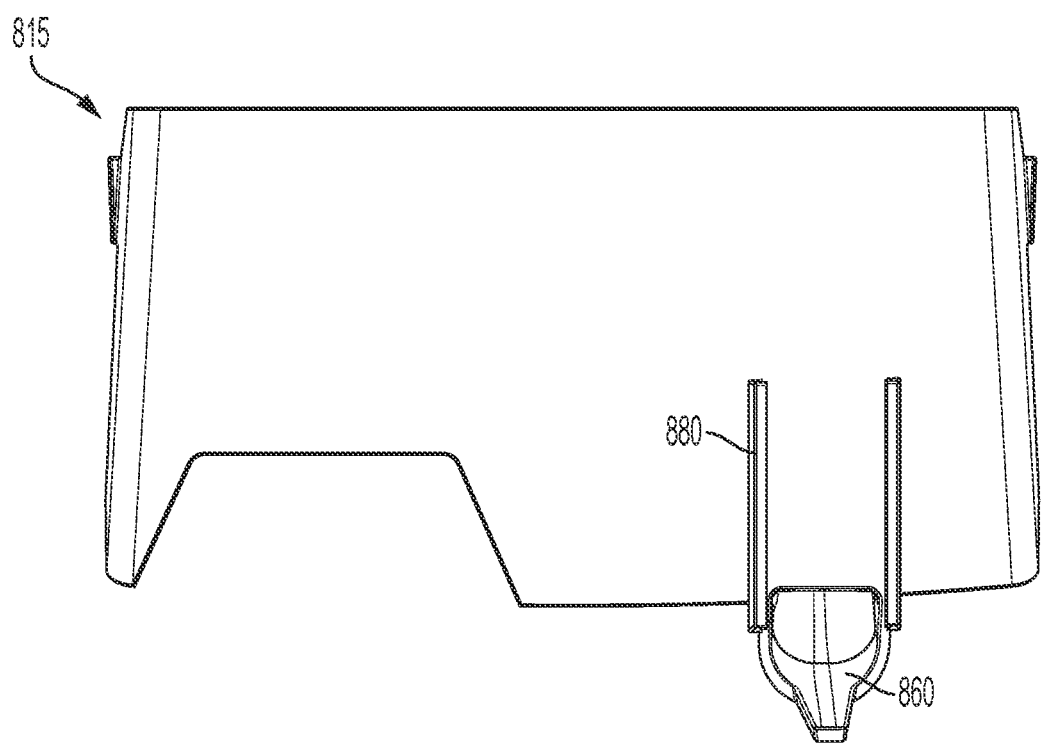
FIG. 13 is a plan view of a front panel of the pharmaceutical counting device of FIG. 10 in accordance with some embodiments.
Figure 14:
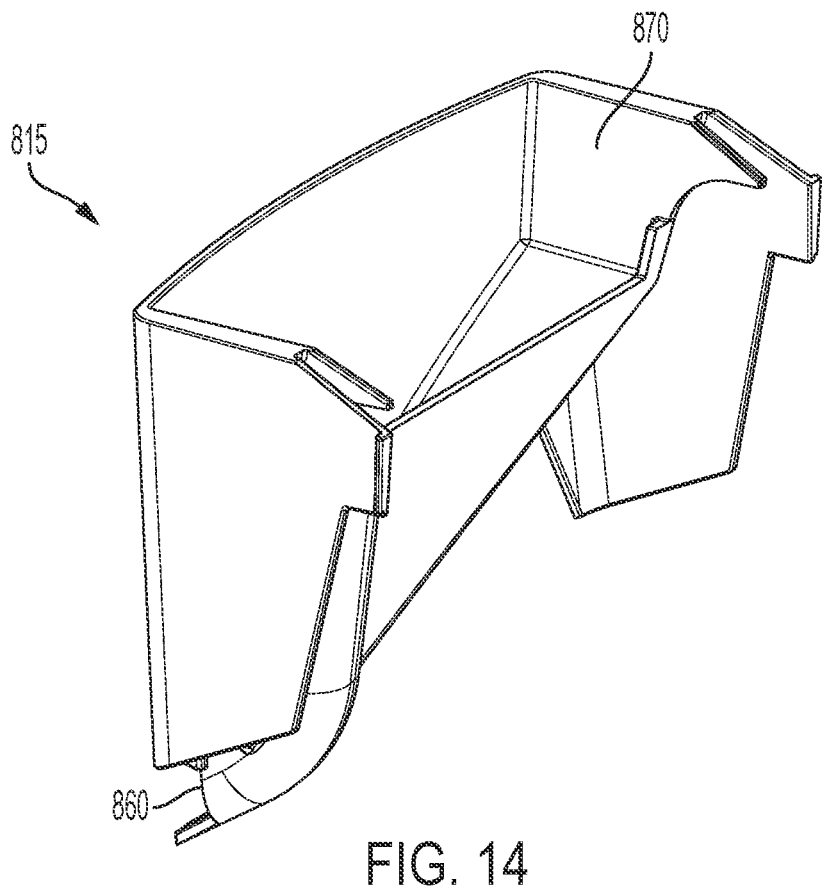
FIG. 14 is a perspective view of the front panel of FIG. 13 in accordance with some embodiments.

Referring to FIGS. 13-14, the front panel 815 is provided at a front of the base portion 810 and includes a spout 860 and a panel funnel 870. In some embodiments, the pharmaceutical counting device 800 is used to fill vials. In these embodiments, the vial may be placed at the spout 860 to be filled with the counted medications on the tray 830. When the medications on the tray 830 are counted, the tray 830 may be lifted towards the front panel 815 such that the medications on the tray 830 are directed to the panel funnel 870. The panel funnel 870 is provided between the counting tray 830 and the spout 860 and slants towards the spout 860 to direct medications in the panel funnel 870 into a vial placed at the spout 860. The front panel 815 is made of transparent or translucent plastic material such that a user may observe the flow of medications from the tray 830 to the vial and ensure that no medications are stuck in the front panel 815. Additionally, the front panel 815 is removably attached to the pharmaceutical counting device 800 such that the front panel 815 may be easily removed for cleaning and servicing. In some embodiments, an opening cover 875 (FIG. 10) is provided on the front panel 815. The opening cover 875 may be moved between a first position that closes the spout 860 such that any medications are stopped from falling out of the spout 860 and a second position that opens the spout 860 such that the medications can flow out of the spout 860. The opening cover 875 moves between the first position and the second position using a sliding mechanism 880 such that the opening cover 875 can slide from the first position to the second position when an upward force is applied on the opening cover 875. The opening cover 875 returns to and rests in the first position when no upward force is applied on the opening cover 875.

Figure 15:
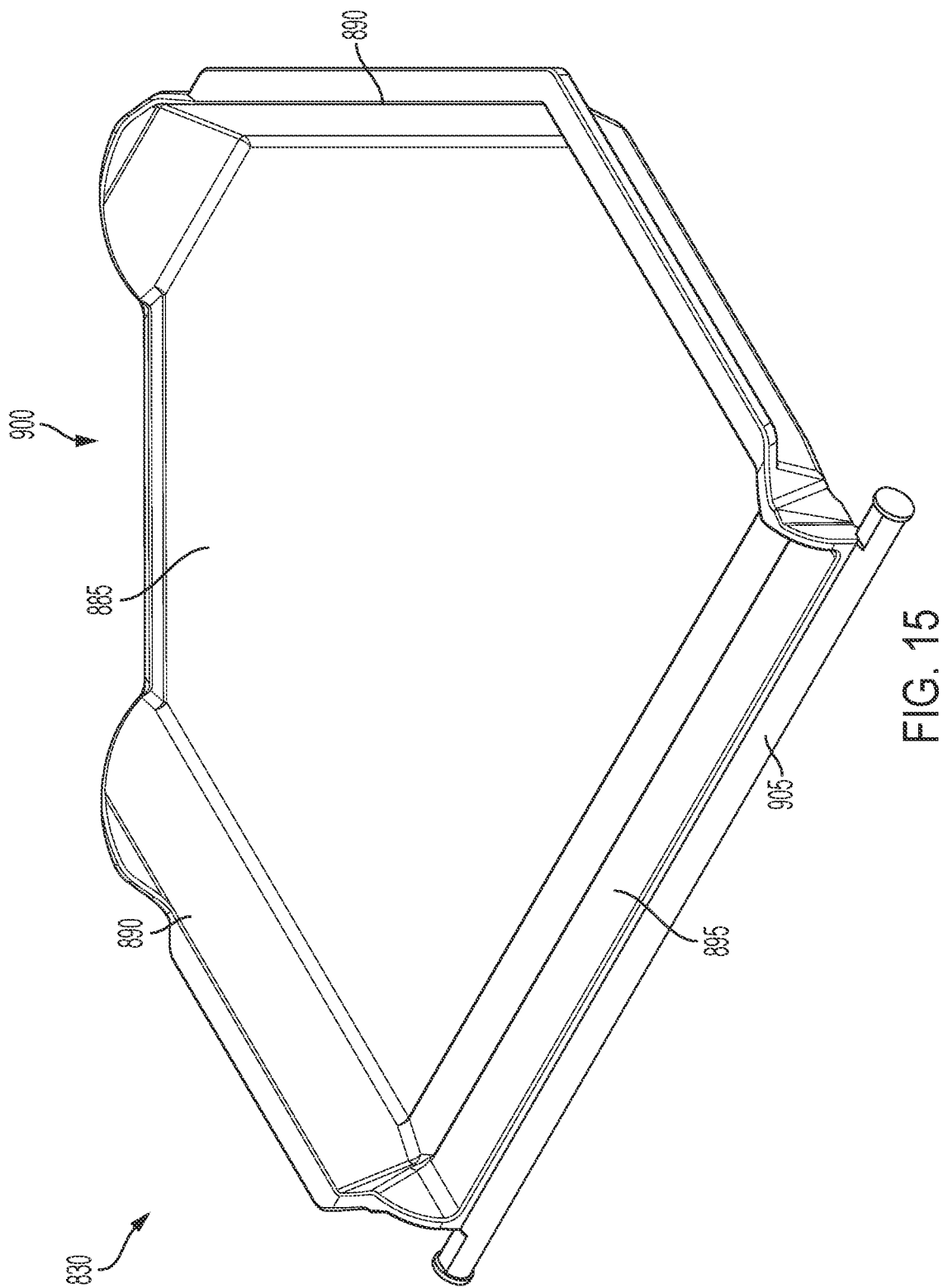
FIG. 15 is a perspective view of a tray of the pharmaceutical counting device of FIG. 10 in accordance with some embodiments.

Referring to FIGS. 10 and 15, the tray 830 is positioned above the base portion 810 and between the front panel 815 and the back panel 820. The tray 830 is provided on and supported by the base portion 810. The tray 830 may be made of opaque or translucent plastic material such that the visible light from the light panel 845 does not pass through the tray 830. In some embodiments, the tray 830 is made of translucent plastic material and includes a set of lights below the tray 830 such that the contents of the tray 830 may be illuminated from below the tray 830. In some embodiments the tray 830 may be made of transparent material with an opaque or translucent diffuser 882 provided below the tray 830 in the base portion 810. The diffuser 882 diffuses the light provided below the diffuser to provide a more even light distribution for the tray 830. The tray 830 rests above the rubber stoppers provided on the base portion 810 such that the tray 830 is provided above the diffuser 882. The tray 830 is configured to receive medications for counting by a camera system 950 (see FIG. 19).

Referring to FIG. 15, the tray 830 is shaped, for example, like a baseball home plate and includes a plate portion 885 with side walls 890 rising from the plate portion 885. The side walls 890 include a front opening 895 and a back opening 900. The tray 830 includes a front hinge 905 that is mounted to a corresponding feature on the base portion 810. The tray 830 may be lifted along the front hinge such that medications on the tray 830 flow through the front opening 895 into the panel funnel 870 of the front panel 815. The tray 830 may also be lifted towards a back side portion such that the medications on the tray 830 may be emptied through the back opening 900 into a cartridge 985 received in the pharmaceutical counting device 800.

Figure 16:
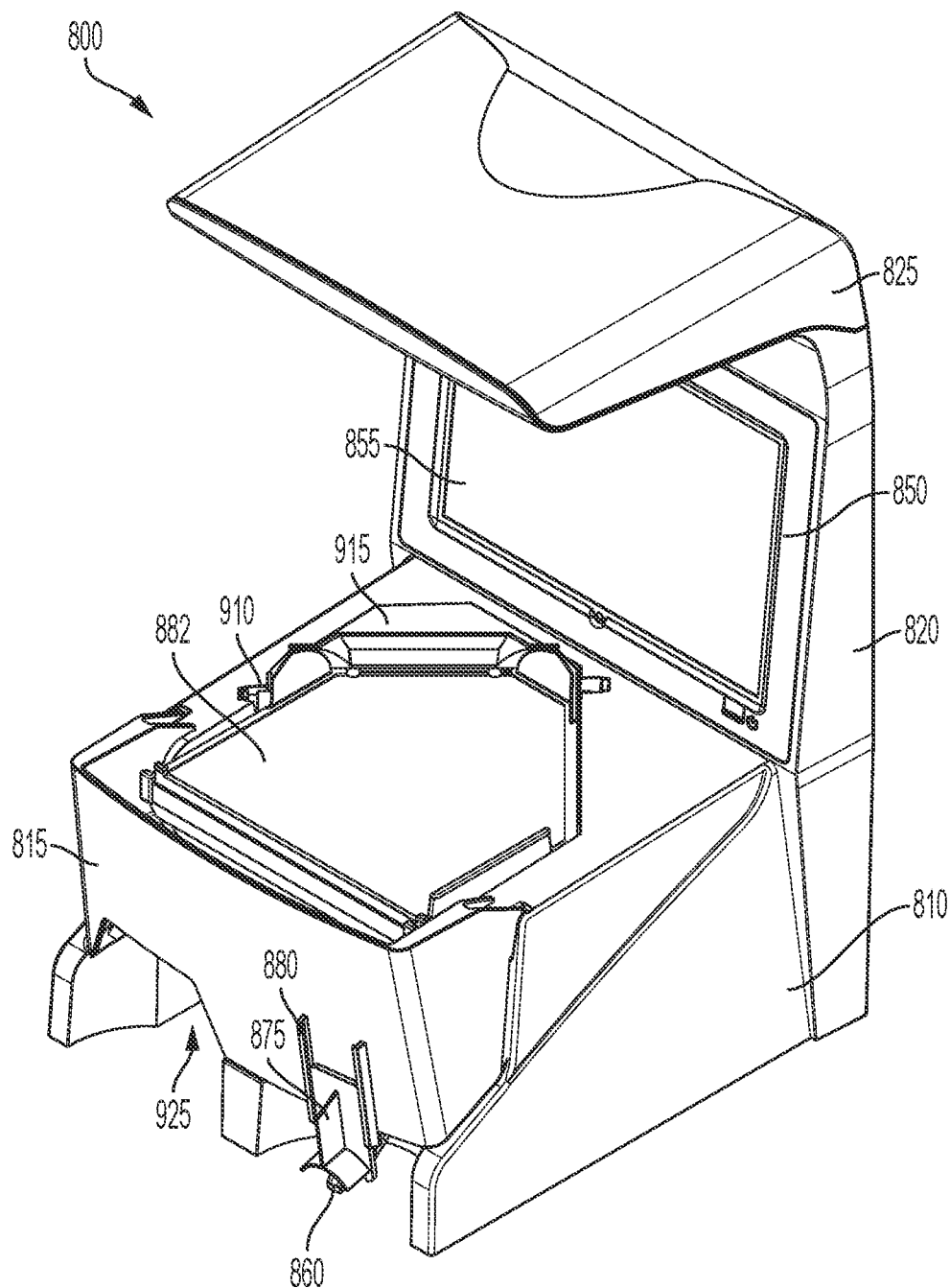
FIG. 16 is a perspective view of the pharmaceutical counting device of FIG. 10 with a tray removed in accordance with some embodiments.

The base portion 810 houses the electrical components of the pharmaceutical counting device 800. In some embodiments, the electrical components may be distributed between the base portion 810, the back panel 820, and the top panel 825. The base portion 810 supports the tray 830, for example over a diffuser 882 (FIG. 16). Referring to FIGS. 10 and 16-18, the base portion 810 includes a tray tilter 910, a slot cover 915, a slot funnel 920 below the slot cover 915 and the tray tilter 910, and a cartridge receiving slot 925 below the slot funnel 920. In some embodiments, a large portion of the electrical components are provided within the tray tilter 910 including, for example, light controls of the diffuser 882, solenoid, solenoid control, vibration motor, vibration motor control, accelerometer, and other sensors. This arrangement allows for the slot funnel 920 to be located directly under the lighting for the tray 830. As a consequence, this arrangement allows changes in the size (e.g., height) of the pharmaceutical counting device 800 and for easy vibration of the entire tray 830. The electrical components may be connected to rest of the pharmaceutical counting device 800 using a standard USB cable.

Figure 17A:
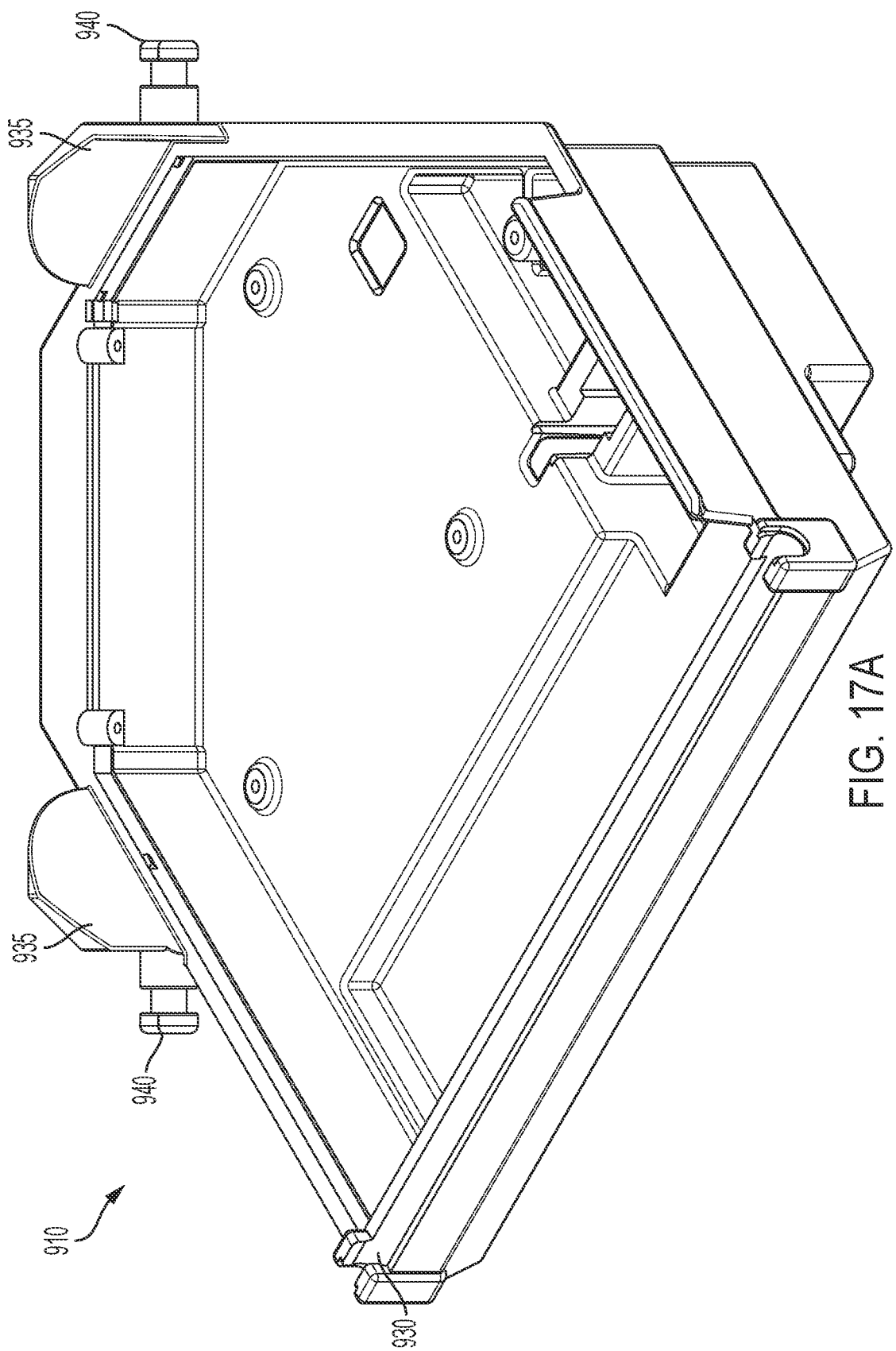
FIGS. 17A and 17B are perspective views of a tray tilter of the pharmaceutical counting device of FIG. 10 in accordance with some embodiments.
Figure 17B:
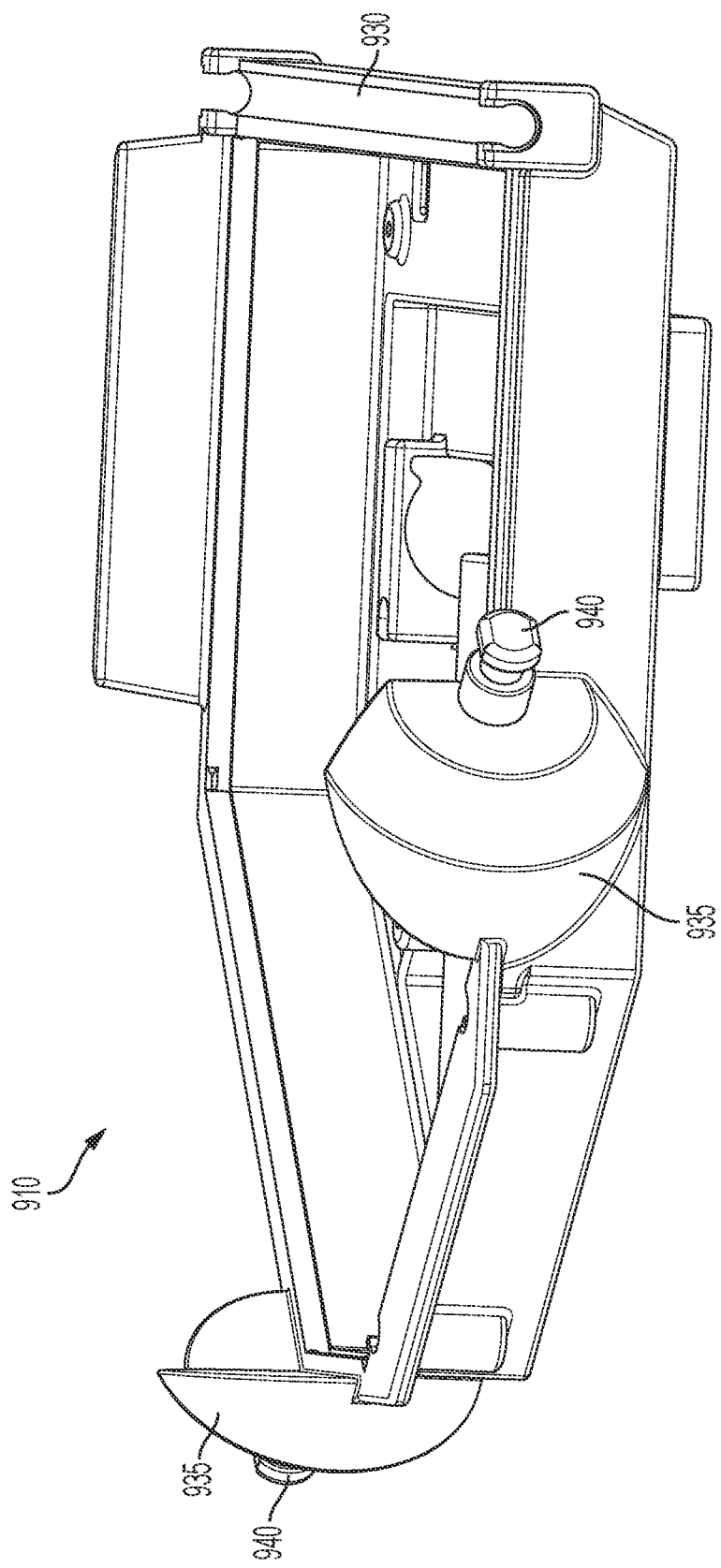

The tray tilter 910 is provided on the base portion 810 and supports the tray 830. Referring to FIGS. 17A and 17B, the tray tilter 910 includes hinge receiving portion 930 that correspondingly receives the front hinge 905 of the tray 830. The hinge receiving portion 930 defines a first axis. The front hinge 905 rotates on the hinge receiving portion 930 about the first axis such that the tray 830 may be lifted to empty the medications on the tray 830 into the panel funnel 870. The tray tilter 910 includes back guides 935 provided at the back and side portions of the tray tilter 910 along the back opening 900 of the tray 830. The back guides 935 include hinge extensions 940 extending laterally outward from the back rollers 935. The back guides 935 define a second axis. The back guides 935 and the hinge extensions 940 are received in corresponding features of the base portion 810. The back guides 935 and the hinge extensions 940 rotate on the base portion 810 about the second axis such that tray tilter 910 along with the tray 830 may be lifted to empty the medications on the tray 830 into the slot funnel 920. Accordingly, the tray 830 may be tilted relative to the tray tilter 910 about the first axis to empty the counted medications into a vial (for example, a first package), and the tray tilter 910 (with the tray 830) may be tilted relative the base portion 810 about the second axis to empty the counted medications into a cartridge 985 (for example a second package of a different kind than the first package) received in the cartridge receiving slot 925. In the illustrated embodiment, the first axis and the second axis are obliquely angled relative to each other. In other embodiments, the first axis may be parallel to the second axis, or may be perpendicular to the second axis. In some embodiments, the back guides 935 and the hinge extensions 940 eliminate potential operator finger pinch points and improve aesthetics.

Figure 18:
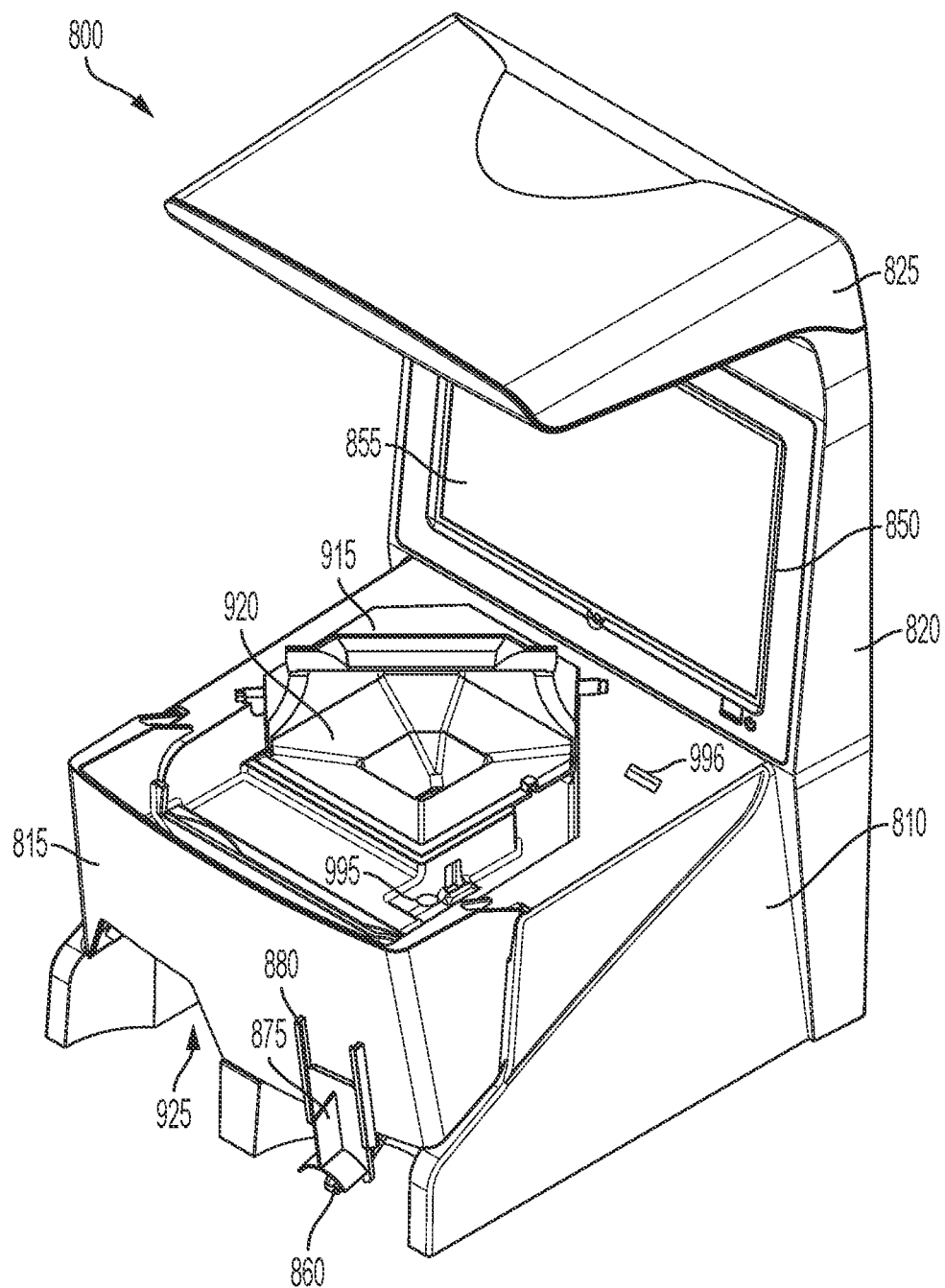
FIG. 18 is a perspective view of the pharmaceutical counting device of FIG. 10 with a tray and tray tilter removed in accordance with some embodiments.

Referring to FIG. 18, the slot cover 915 blocks the back opening 900 of the tray 830 such that medications cannot flow into the slot funnel 920 when the tray tilter 910 is not lifted. In some embodiments, a solenoid lock, or other lock mechanism 916 (see FIG. 19), may be provided on the slot cover 915 such that the slot cover 915 is locked in place to prevent the tray tilter 910 from being lifted to empty the medications into the cartridge 985. In some embodiments, the solenoid lock 916 may be provided at the tray tilter 910 such that the tray tilter 910 may not be opened. The solenoid lock 916 may be activated to lock the slot cover 915 or the tray tilter 910 (and therefore, the tray 830) when an incorrect type and/or number of medications are placed on the tray 830. The solenoid lock 916 may be deactivated to allow the tray tilter 910 to be lifted when the correct type and/or number of medications are placed on the tray 830. A method for activating and deactivating the solenoid lock 916 is provided below with respect to FIG. 21. The slot funnel 920 directs the medications from the tray 830 to the cartridge 985 received in the cartridge receiving slot 925 when the tray tilter 910 is lifted. The tray tilter 910, the slot cover 915, and the slot funnel 920 are removably attached to the base portion 810 such that the tray tilter 910, the slot cover 915, and the slot funnel 920 may be removed for cleaning and servicing. In some embodiments, the front panel 815, the tray tilter 910, the slot cover 915, and the slot funnel 920 are made of suitable plastic material to facilitate hand-cleaning and/or to facilitate cleaning in a dishwasher.

Referring to FIG. 18, in some embodiments, a magnet 995 is provided below the tray tilter 910 on the base portion 810. A corresponding metal portion may be provided on the tray tilter 910 such that the magnet 995 holds down the tray tilter 910 in place and reduces unintended vibrations of the tray tilter 910 and/or the tray 830. In one example, the magnet 995 is a permanent magnet. In other examples, the magnet 995 is an electric magnet that is electrically actuated to hold down the tray tilter 910. In some embodiments, the magnet 995 and the corresponding metal portion may be interchanged such that the magnet 995 is provided at the bottom of the tray tilter 910 with the corresponding metal portion provided below the tray tilter 910 on the base portion 810.

In some embodiments, the base portion 810 is also provided with a data port 996 (see FIG. 18). The data port 996 may receive, for example, a scanner 997 (see FIG. 10). The scanner 997 may be a biometric scanner, for example, a finger print scanner. The scanner 997 may be used to provide an alternative login method to login to the pharmaceutical counting device 800. The data port 996 may be a Universal Serial Bus (USB) port (e.g., USB 2.0, USB 3.0, or the like). The data port 996 may also receive a data transfer device such that transaction data from the pharmaceutical counting device 800 may be transferred to the data transfer device. In some embodiments, the scanner 997 may be secured to the data port 996 (e.g., by fasteners, brackets, etc.) to inhibit removal of the scanner 997 from the data port 996 and, thereby, unauthorized access of the data port 996.

Figure 19:
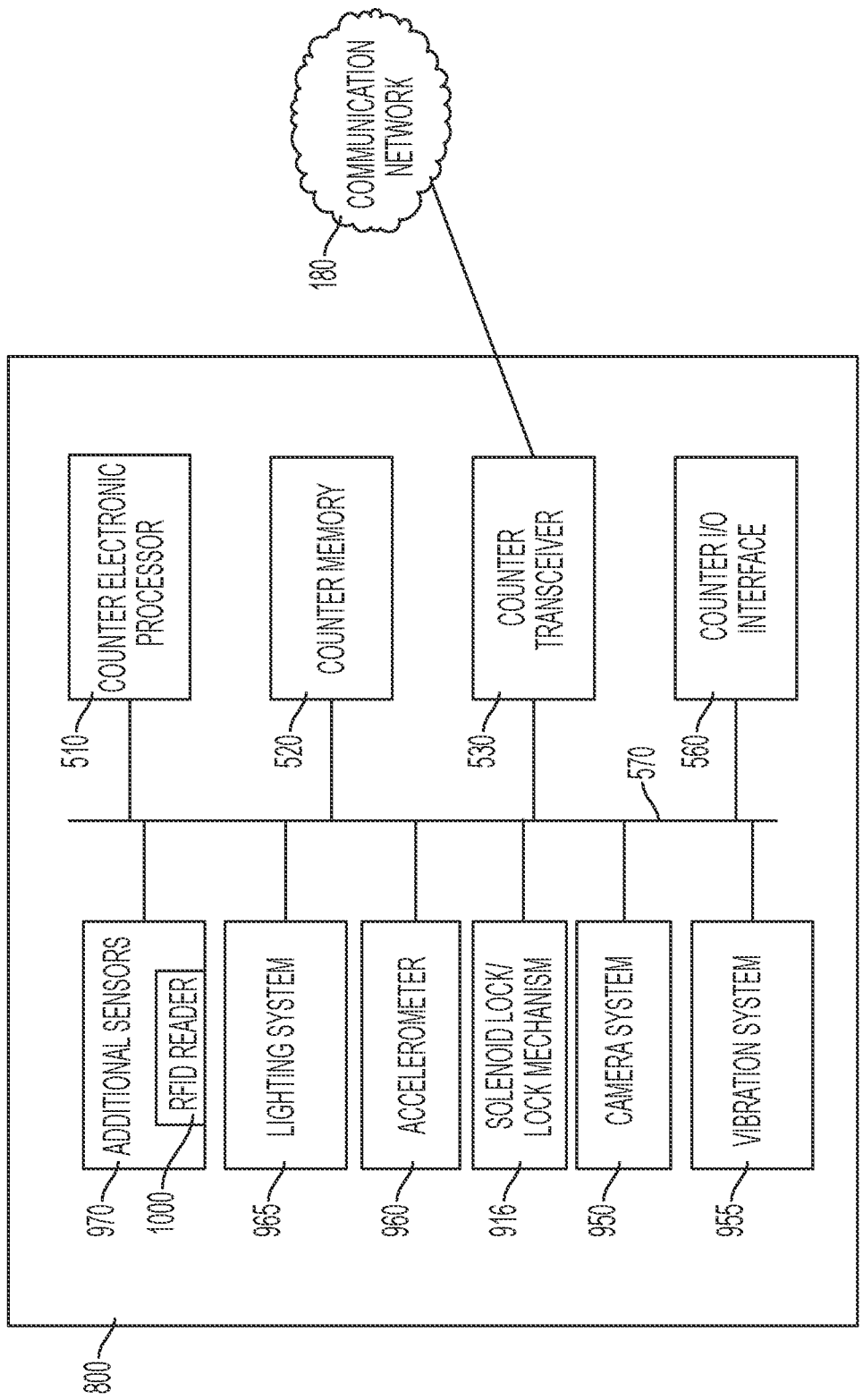
FIG. 19 is a schematic of the pharmaceutical counting device of FIG. 10 in accordance with some embodiments.

FIG. 19 schematically illustrates the pharmaceutical counting device 800 and its functionality within a pharmacy. In the example illustrated, the pharmaceutical counting device 800 includes the counter electronic processor 510, the counter memory 520, the counter transceiver 530, a camera system 950, a vibration system 955, an accelerometer 960, a lighting system 965, and the counter input/output interface 560. The counter electronic processor 510, the counter memory 520, the counter transceiver 530, the camera system 950, the vibration system 955, the accelerometer 960, and the counter input/output interface 560 communicate over one or more control and/or data buses (e.g., the communication bus 570). FIGS. 10-19 illustrate only one exemplary embodiment of the pharmaceutical counting device 800. The pharmaceutical counting device 800 may include more or fewer components and may perform functions other than those explicitly described herein.

The camera system 950 includes the top camera 842, the barcode sensor 840, and the camera of the display device 855. The counter electronic processor 510 controls the camera system 950 similarly as described in the method 600 to identify and count the medications on the tray 830. The counter electronic processor 510 controls the camera system 950 (that is, the barcode sensor 840) to verify that a correct bulk storage container is used for the prescription currently being filled. Additionally, the counter electronic processor 510 may also control the camera system 950 (that is, the barcode sensor 840) to verify that a correct package is being packaged by the pharmaceutical counting device 800. In some embodiments, the barcode scanner 840 is a two-dimensional color camera which may also be used to capture images of the pills on the tray 830. The barcode scanner 840 can be used in conjunction with the top camera 842 to generate stereoscopic three-dimensional information of the tray 830 to obtain three-dimensional information of the medications on the tray 830. Other three-dimensional imaging systems, for example, laser based imaging systems, visual light based imaging system, and the like may be used to generate three-dimensional representations of the medications under inspection.

The vibration system 955 includes a vibrating motor or similar vibration mechanism provide in the tray tilter 910. The counter electronic processor 510 controls the vibration system 955 to vibrate the tray 830. The lighting system 965 includes the light panel 845 and the lights provided under the diffuser 882. The counter electronic processor 510 controls the lighting system 965 similarly as described in the method 600 to capture images of the contents of the tray 830.

The vibration system 955 may be user activated or activated automatically by the counter electronic processor 510 based on certain conditions. For example, a user may actuate a switch to trigger the vibration system 955. The vibration system 955 vibrates the tray 830 to separate any medications that may be sticking together or overlapping (e.g., resting at least partially on top of each other) resulting in an error in identifying or counting the medications on the tray 830. In some embodiments, the counter electronic processor 510 may recognize the error and automatically activate the vibration system 955 to separate the pill. The counter electronic processor 510 may continue to vibrate the tray 830 until the error is resolved. In other embodiments, the counter electronic processor 510 may vibrate the tray 830 in short bursts (e.g., 1 second bursts) until the error is resolved.

The accelerometer 960 may be provided in the tray 830 or in the tray tilter 910. The counter electronic processor 510 receives signals from the accelerometer 960 to detect an orientation of the tray 830. The counter electronic processor 510 may monitor the accelerometer 960 to ensure that the pills are emptied into the vial or the cartridge 985. In some embodiments, the counter electronic processor 510 may monitor the accelerometer 960 to ensure that the tray 830 is level such that the medications do not roll off the tray 830. The counter electronic processor 510 may provide an indication of the level on the display device 855. The pharmaceutical counting device 800 may include levelling screws or feet that can attach to the removable base 805 or the base portion 810 to adjust a level of the pharmaceutical counting device 800. In some embodiments, the accelerometer 960 is used to ensure that the user is lifting the tray 830 properly. If the tray 830 is lifted too fast, the medications on the tray 830 may be thrown off outside the pharmaceutical counting device 800. The accelerometer 960 therefore verifies that the tray 830 is not lifted too fast. In some embodiments, the accelerometer 960 is used to ensure that the vibration system 955 is functioning correctly. For example, the counter electronic processor 510 may verify that the vibration system 955 was activated by monitoring the accelerometer 960 readings.

The pharmaceutical counting device 800 may include additional sensors 970 (for example, optical sensors, magnetic sensors, and the like) to verify other components of the pharmaceutical counting device 800. For example, funnel sensors may be provided to detect whether the panel funnel 870 and the slot funnel 920 are in the correct position when the pharmaceutical counting device 800 is being operated. Tilting sensors may be used to detect whether the tray 830 has been tilted past a predetermined point. The predetermined point may be selected to be a point at which the medications on the tray 830 slide off tray 830 into the panel funnel 870 or the slot funnel 920. The additional sensors 970 may also include a biometric operator identification sensor and/or an RFID reader 1000. The biometric operator identification sensor may include a fingerprint sensor to identify an operation using a fingerprint of the user, or a camera to identify a user using facial recognition. The RFID reader may be used to identify a bulk storage container used for filling a prescription and/or to identify a package being packaged or filled by the pharmaceutical counting device 800. In one example, the RFID reader 1000 is provided in the cartridge receiving slot 925 to read an RFID tag of a cartridge 985 received in the cartridge receiving slot 925. The RFID reader 1000 is positioned such that the RFID reader 1000 aligns with an RFID tag of the cartridge 985 when the cartridge 985 is inserted into the cartridge receiving slot 925. The RFID reader 1000 provides additional verification to ensure that the correct cartridge 985 (for example, a cartridge 985 for receiving the correct kind of medication) is received in the cartridge receiving slot 925. In some embodiments, one or more of the barcode sensor 840 and the additional sensors 970 form the verification system for verifying that a correct package is being used by the pharmaceutical counting device 800.

Figure 20:
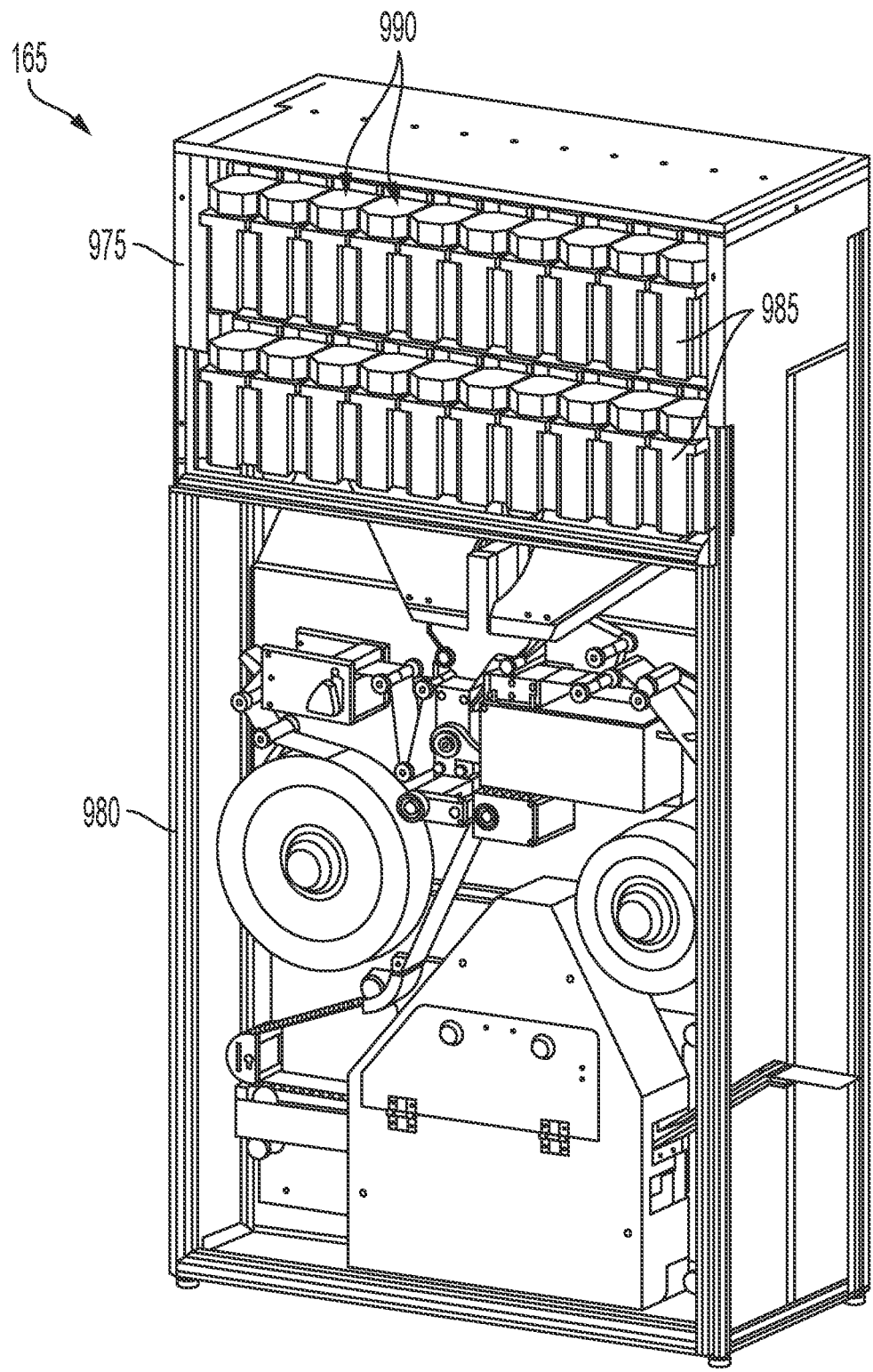
FIG. 20 is a perspective view of an automatic packager of the pharmacy management system of FIG. 1 in accordance with some embodiments.

FIG. 20 illustrates an example automatic packager 165 including a universal feed cassette 975 and a packaging unit 980 according to an example embodiment. The universal feed cassette 975 receives medications from the bulk canisters or the pharmaceutical counting device 800 and individually dispenses pills to the packaging unit 980. Each universal feed cassette 975 may dispense eight to ten separate pills at the same time. In other embodiments, the universal feed cassette 975 may dispense sixteen, twenty, or more separate pills at the same time. In some embodiments, the automatic packager 165 may include more than one universal feed cassette 975.

The universal feed cassette 975 includes a plurality of cartridges 985 arranged within the housing of the universal feed cassette 975. In one example, the universal feed cassette 965 may include up to ten cartridges 985 that are received in cartridge slots 990. In another example, the universal feed cassette 975 may include up to twenty cartridges 985 that are received in the cartridge slots 990. For example, the cartridges 985 may be received in two levels or tiers of cartridge slots 990. A pharmacist may load medications from bulk canisters or the pharmaceutical counting device 800 into each of the cartridges 985 as set forth above. The same medications may be loaded into each cartridge 985, or different medications may be loaded into each cartridge 985. The cartridges 985 independently dispense the medications to the packaging unit 980.

The cartridges 985 are removably fixed to the universal feed cassette 975. A pharmacist or technician may remove each individual cartridge 985 from the cartridge slot 990 to fill the cartridge 985 with medications from the pharmaceutical counting device 800. In such scenarios, the cartridge 985 can be inserted into the cartridge receiving slot 925 (FIG. 10) of the pharmaceutical counting device 800, and the tray tilter 910 with the tray 830 may be pivoted about the second axis to pour pharmaceuticals on the tray 830 into the cartridge 985. The filled cartridge 985 can then be returned to any of the cartridge slots 990 for packaging by the automatic packager 165.

An example cartridge 985 is described in U.S. patent application Ser. No. 16/160,535, filed on Oct. 15, 2018, entitled "UNIVERSAL FEED MECHANISM FOR AUTOMATIC PACKAGER," the entire contents of which are hereby incorporated by reference. In other embodiments, other suitable cartridges may also or alternatively be used. In the example illustrated in FIG. 7, the packaging unit is a strip packager. An example strip packager is described in U.S. Patent Application Publication No. 2013/031891 and U.S. Patent Application Publication No. 2017/0015445, the entire contents of both of which are hereby incorporated by reference. In other embodiments, other suitable packaging units, including strip packagers, blister card packagers, and the like, may also or alternatively be used.

Figure 21:
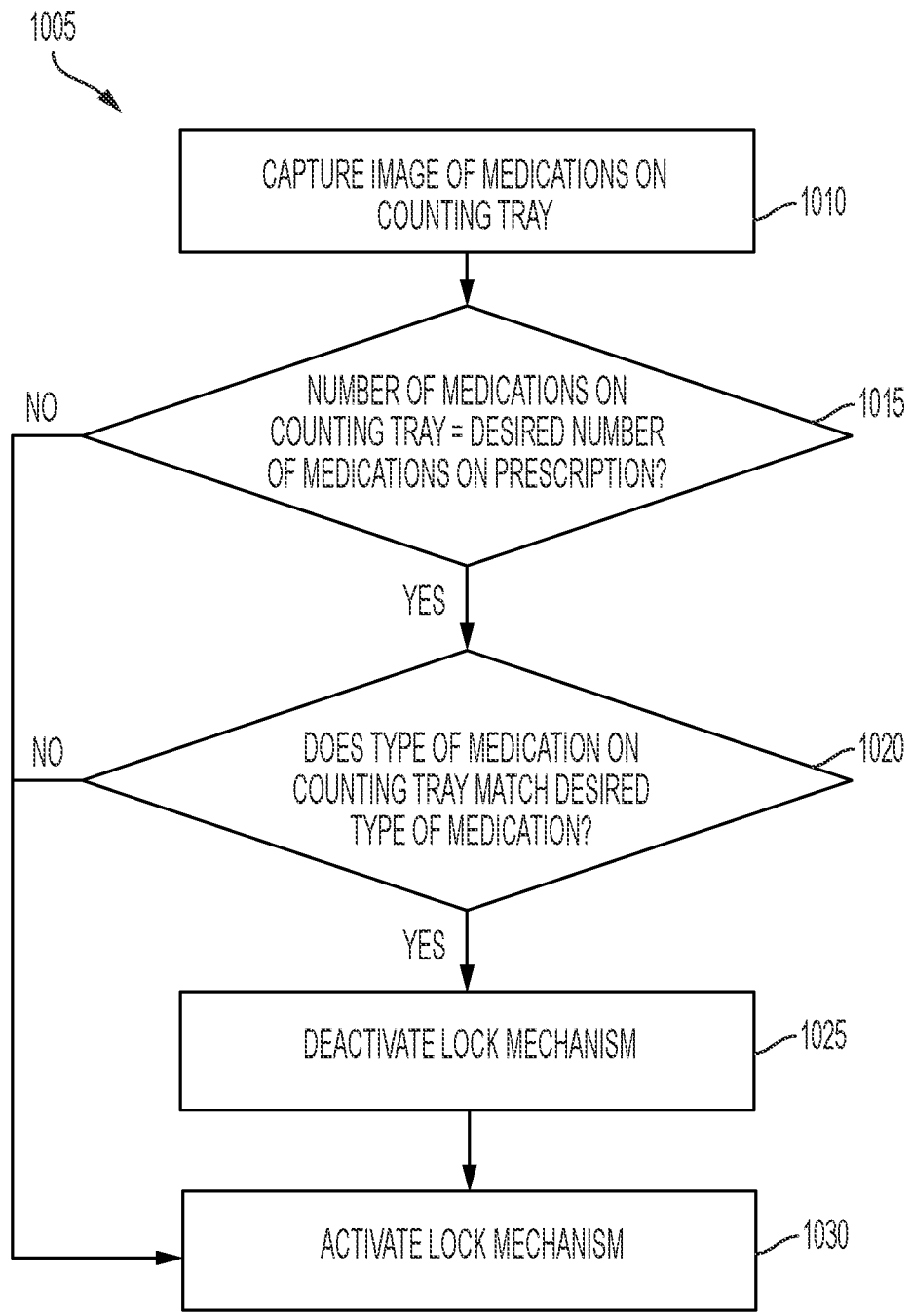
FIG. 21 is a flowchart of a method for controlling a lock mechanism of the pharmaceutical counting device of FIG. 10 in accordance with some embodiments.

FIG. 21 depicts a method 1005 of controlling a lock mechanism 916 of the pharmaceutical counting device 800. Although the method 1005 includes specific blocks, all the blocks need not be performed or performed in the order presented. At block 1010, the method 1005 includes activating the lock mechanism 916. The lock mechanism 916 is generally activated at startup and is kept activated until the conditions as provided below are satisfied. At block 1015, the method 1005 includes capturing, using the camera system 950, and image of the medications on the tray 830. The counter electronic processor 510 controls the lighting system 965 to illuminate the contents of the tray and controls the top camera 842 to capture an image of the contents of the tray 830.

At block 1020, the method 1005 includes determining whether a number of medications on the tray 830 matches a desired number of medications provided on a prescription being filled by the pharmaceutical counting device 800. As discussed above, the pharmacy management system 100 receives a prescription to be filled. The pharmacy management system 100 provides the information regarding the prescription including the types of medications and the number of medications for each type of medications to be filled for the prescription to the pharmacy counting device 800. The counter electronic processor 510 analyzes the captured image of the contents of the tray 830 to count the number of medications on the tray 830. Specifically, the electronic processor 510 uses image recognition techniques to determine objects in the image and identifies the number of objects in the image to determine the number of medications on the tray 830. The counter electronic processor 510 compares the number of medications on the tray 830 to the desired number of medications to determine whether the number of medications on the tray 830 match the desired number of medications.

At block 1025, the method 1005 includes determining whether a type of medication on the tray 830 matches a desired type of medication provided on the prescription. The counter electronic processor 510 analyzes the captured image of the contents of the tray 830 to determine the type of medication on the tray. Specifically, the counter electronic processor 510 uses image recognition techniques to determine objects in the image. The counter electronic processor 510 then extracts characteristics of the objects, for example, a size (e.g., diameter, length, width, and the like), a shape, a color, indications on the object, and/or the like. The counter electronic processor 510 then compares the characteristics of each medication with the characteristics of the desired medication. The characteristics of the desired medications may be obtained from the national drug code (NDC) database. In some embodiments, the characteristics of the desired medications are obtained using training data. That is, the counter electronic processor 510 learns the characteristics of the medications as the medications are being counted using the pharmaceutical counting device 800. The counter electronic processor 510 compares the characteristics of the medication on the tray 830 to the characteristics of the expected type of medication to determine whether the type of medication on the tray 830 matches the desired type of medication.

The method 1005 returns to block 1010 to keep the lock mechanism 916 activated when either the number of medications does not match the desired number of medications or the type of medication does not match the desired type of medication, or both. The counter electronic processor 510 maintains the solenoid lock 916 (that is, locks the solenoid lock 916) in a locked state to keep the slot cover 915 closed or to inhibit the tray tilter 910 (and therefore, the tray 830) from being lifted to empty the medications into a package.

At block 1030, the method 1005 includes deactivating the lock mechanism when the number of medications matches the desired number of medications and the type of medication matches the desired type of medication. The counter electronic processor 510 deactivates the solenoid lock 916 (that is, unlocks the solenoid lock 916) to allow the slot cover 915 to open or to allow the tray tilter 910 (and therefore, the tray 830) to be lifted to empty the medications into a package.

Figure 22:
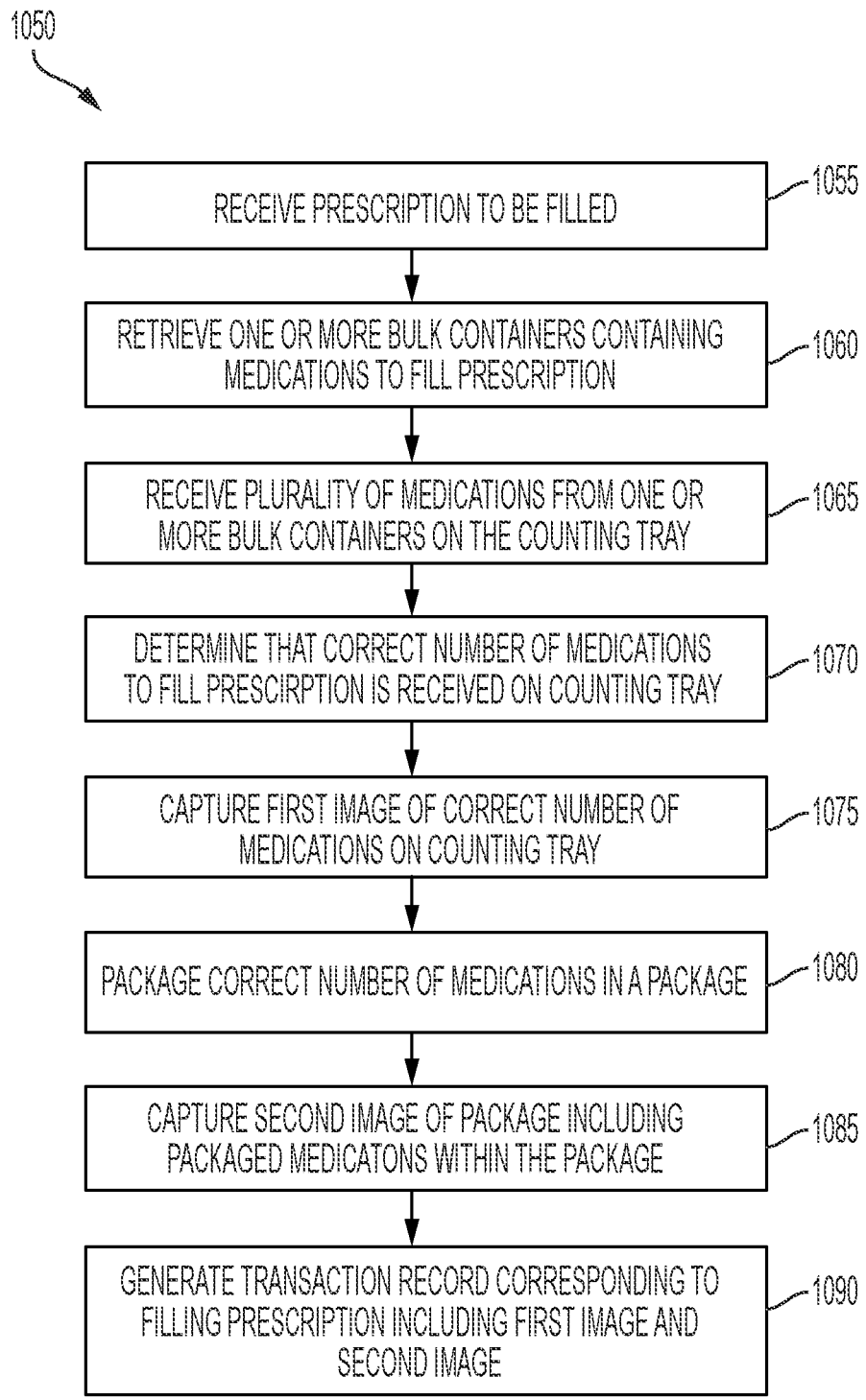
FIG. 22 is a flowchart of a method for packaging medications using the pharmaceutical counting device of FIG. 10 in accordance with some embodiments.

FIG. 22 depicts a method 1050 for packaging medications using the pharmaceutical counting device 800. Although the method 1050 includes specific blocks, all the blocks need not be performed or performed in the order presented. The method 1050 leverages the automated nature of the pharmacy to verify the correct type and/or number of pharmaceuticals are loaded into each package as part of filling a prescription. The package may take any form, for example, a pouch package, a blister card package, a pill vial, and the like. In particular, the method 1050 involves providing a transaction record for a pharmacist to verify filling the prescription from when the prescription is received until the pharmaceuticals are loaded and sealed in a package to create a chain of custody for the pharmaceuticals. The transaction record may be stored as an electronic file in the memory 120 of the pharmacy management system 100, in the counter memory 520, or the memory of a remote computer or server.

At block 1055, the method 1050 includes receiving, at the pharmacy management system 100, a prescription to be filled. In one embodiment, the prescription may be received electronically through the communication network 180 from a healthcare facility. In other embodiments, the prescription may be received by scanning a paper prescription presented by a customer or by manually entering the contents of the prescription presented by the customer into the pharmacy management system 100.

At block 1060, the method 1050 includes retrieving bulk storage containers containing the medication needed to fill the prescription. As described above, the pharmaceutical storage and retrieval system 150 retrieves the containers including the medications for the prescription to be picked up by the pharmacist in response to receiving or scanning the information sheet at the pharmaceutical storage and retrieval system 150. In other embodiments, the pharmacist may manually retrieve the containers including the medications from storage shelves of the pharmacy based on an information sheet printed by the pharmacy management system 100.

At block 1065, the method 1050 includes receiving a plurality of medications from the one or more bulk containers on the tray 830. The pharmacist or technician may pour the medications from the bulk container onto the tray 830 for counting. The bulk container may first be scanned using the bar code sensor 840 to verify that the type of medication within the bulk container matches a type of medication on the prescription. The pharmaceutical counting device 800 provides an indication on the display device 855 of whether the bulk container includes the correct type of medication.

At block 1070, the method 1050 includes determining, using the counter electronic processor 510, that a correct number of medications to fill the prescription is received on the tray 830. The method 1050 may also include determining, using the counter electronic processor 510, an expected medication type to be counted using the pharmaceutical counting device 800. Once the plurality of medications from the bulk container are received, the pharmaceutical counting device 800 may prompt, using the display device 855, a user to remove medications from the tray 830 when excess medications or medications of a wrong type are received on the tray 830. The pharmaceutical counting device 800 may provide an indication on the display device 855 to add medication to the tray 830 when fewer than the desired number of medications are received on the tray 830. The pharmaceutical counting device 800 provides an indication on the display device 855 to denote that the correct number and type of medications are received on the tray 830 once the user follows the prompts to provide the correct number and type of medications.

Figure 24:
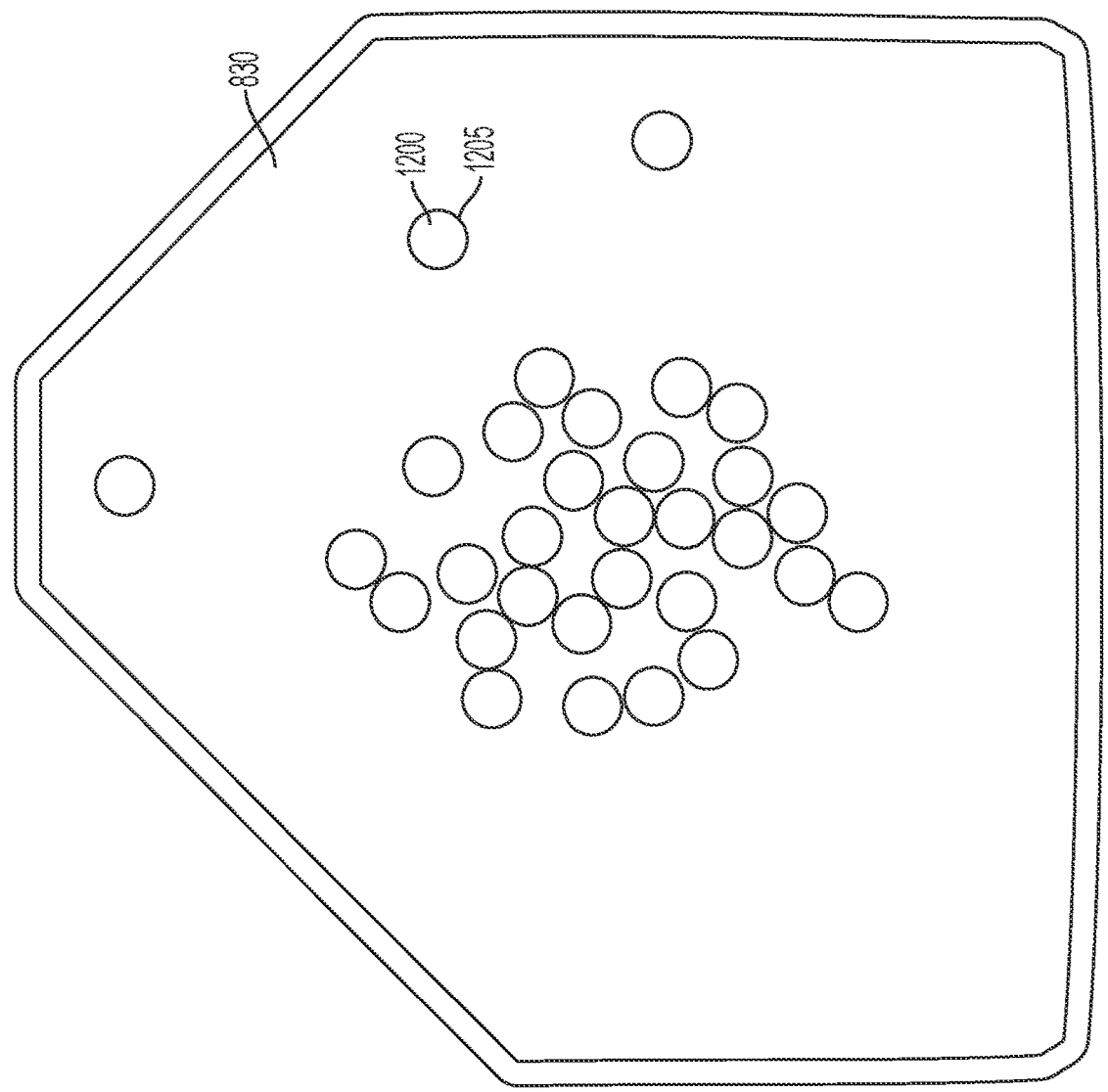
FIG. 24 illustrates an example image captured by a camera system of the pharmaceutical counting device of FIG. 10 in accordance with some embodiments.
Figure 27:
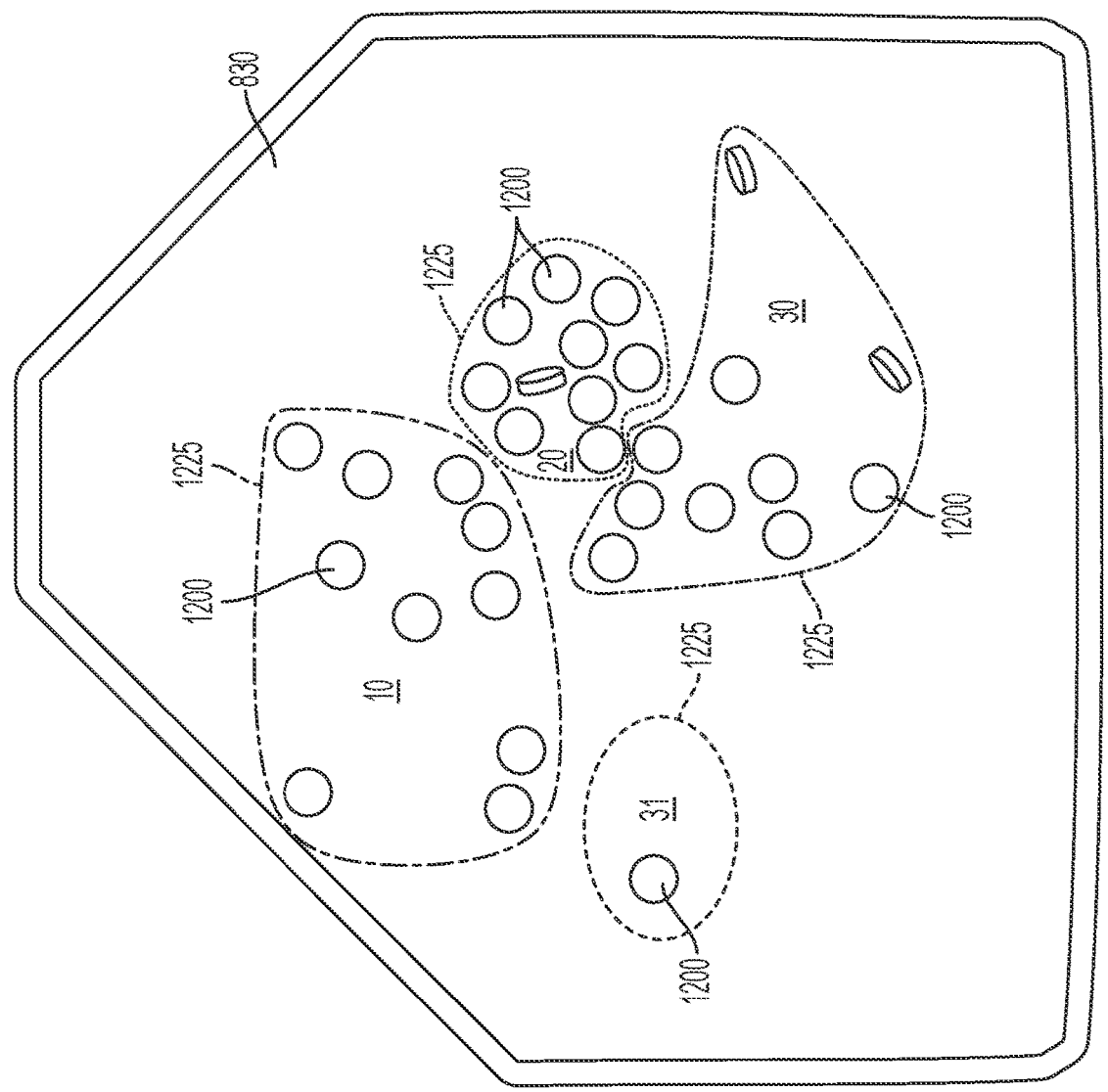
FIG. 27 illustrates an example image captured by a camera system of the pharmaceutical counting device of FIG. 10 in accordance with some embodiments.

At block 1075, the method 1050 includes capturing, using the camera system 950, a first image of the correct number of medications on the tray 830. The counter electronic processor 510 controls the top camera 842 to capture an image of the contents of the tray 830 when the counter electronic processor 510 determines that the correct number of medications are received on the tray 830. One example of the first image is illustrated in FIG. 24. As shown in FIG. 24, the first image illustrates the medications 1200 on the tray 830. In some embodiments, a highlight 1205 is provided around each medication 1200 to indicate whether the medications are of the correct type, that is, the type currently being counted and packaged by the pharmaceutical counting device 800. In some embodiments, the method 1050 also includes displaying, on the display device 55, the first image and overlaying, using the counter electronic processor 510, a plurality of indications on the first image displayed on the display device to facilitate counting of a number of medications. The overlaid indications may group the medications on the tray using color codes. For example, each group of three pills may be assigned a different color, which is overlaid on the group of pills with a first group of three pills overlaid with a first color and a second group of three pills overlaid with a second color. One example of the overlaid image is illustrated in FIG. 27. As shown in FIG. 27, the overlaid image illustrates the medications 1200 on the tray 830. A grouping indicator 1225 is provided around a group of ten medications 1200 to facilitate manual counting of the medications 1200. In other embodiments, the grouping indicators 1225 could be provided around groups of different numbers, such as three medications or five medications.

At block 1080, the method 1050 includes packaging, using the pharmaceutical counting device 800, the correct number of medications in a package. The package is, for example, a pill vial, a cartridge 985 of an automatic packager 165, or the like. The medications are packaged in the pill vial by tilting the tray 830 forward to direct the medications into the pill vial using the spout 860. The medications are packaged in the cartridge 985 by tilting the tray 830 backward to direct the medications into the cartridge using the slot funnel 920.

Figure 25:
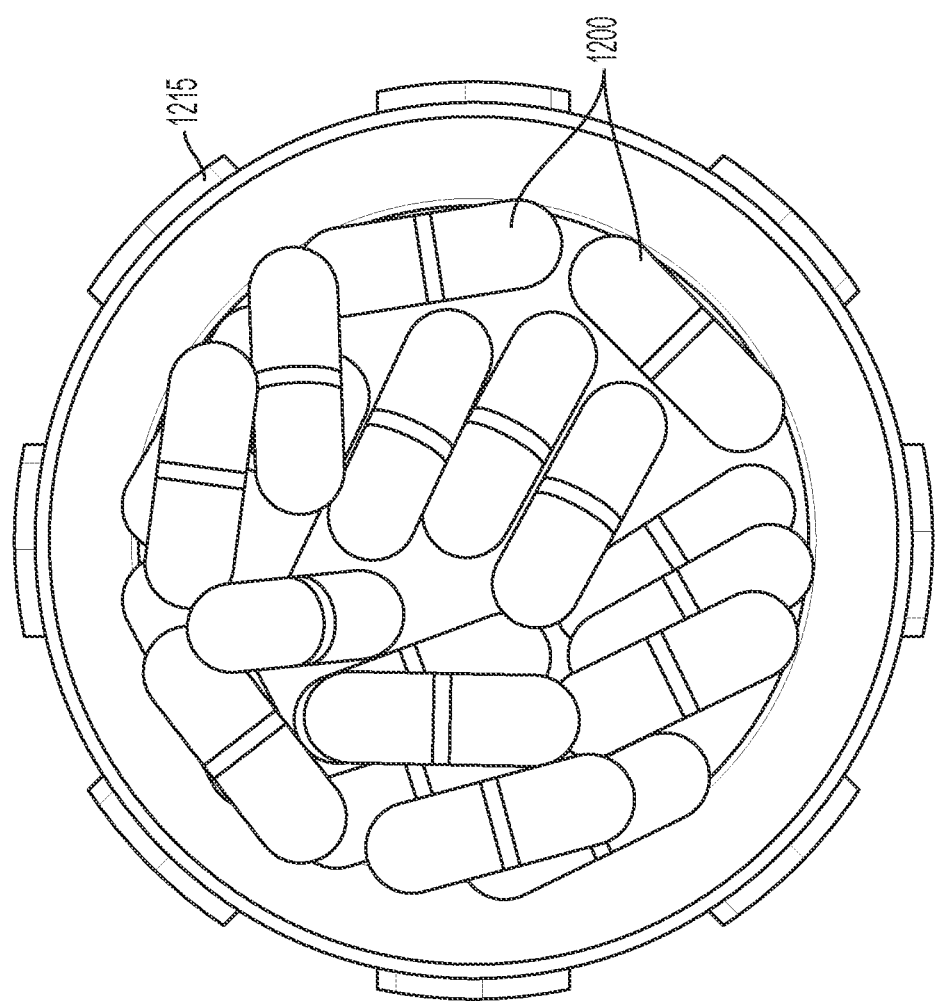
FIG. 25 illustrates an example image captured by a camera system of the pharmaceutical counting device of FIG. 10 in accordance with some embodiments.

At block 1085, the method 1050 includes capturing, using the camera system 950, a second image of the package including packaged medications within the package. Once the medications are packaged, the package may be placed on the tray 830. For example, a pharmacist or technician may place a packaged pill vial (for example, before place the top on) on the tray 830. The counter electronic processor 510 controls the top camera 842 to capture an image of the package. For example, the top camera 842 may capture an image looking into the opening of the pill vial and showing the medications within the pill vial. In some embodiments, the top camera 842 may automatically zoom when the counter electronic processor 510 recognizes that the image being captured is of the pill vial and not the contents of the tray 830. One example of the second image is shown in FIG. 25. As shown in FIG. 25, the second image illustrates the vial 1215 including the plurality of counted medications 1200.

At block 1090, the method 1050 includes generating, using the counter electronic processor 510, a transaction record corresponding to filling the prescription including the first image and the second image. The counter electronic processor 510 generates the transaction record and includes the first image and the second image in the transaction record. The transaction record may be stored as an electronic file in the memory 120 of the pharmacy management system 100, in the counter memory 520, or the memory of a remote computer or server. In some embodiments, the transaction record may be forwarded to, for example, a remote pharmacist within the pharmacy or in a different location for remote verification.

Figure 26:
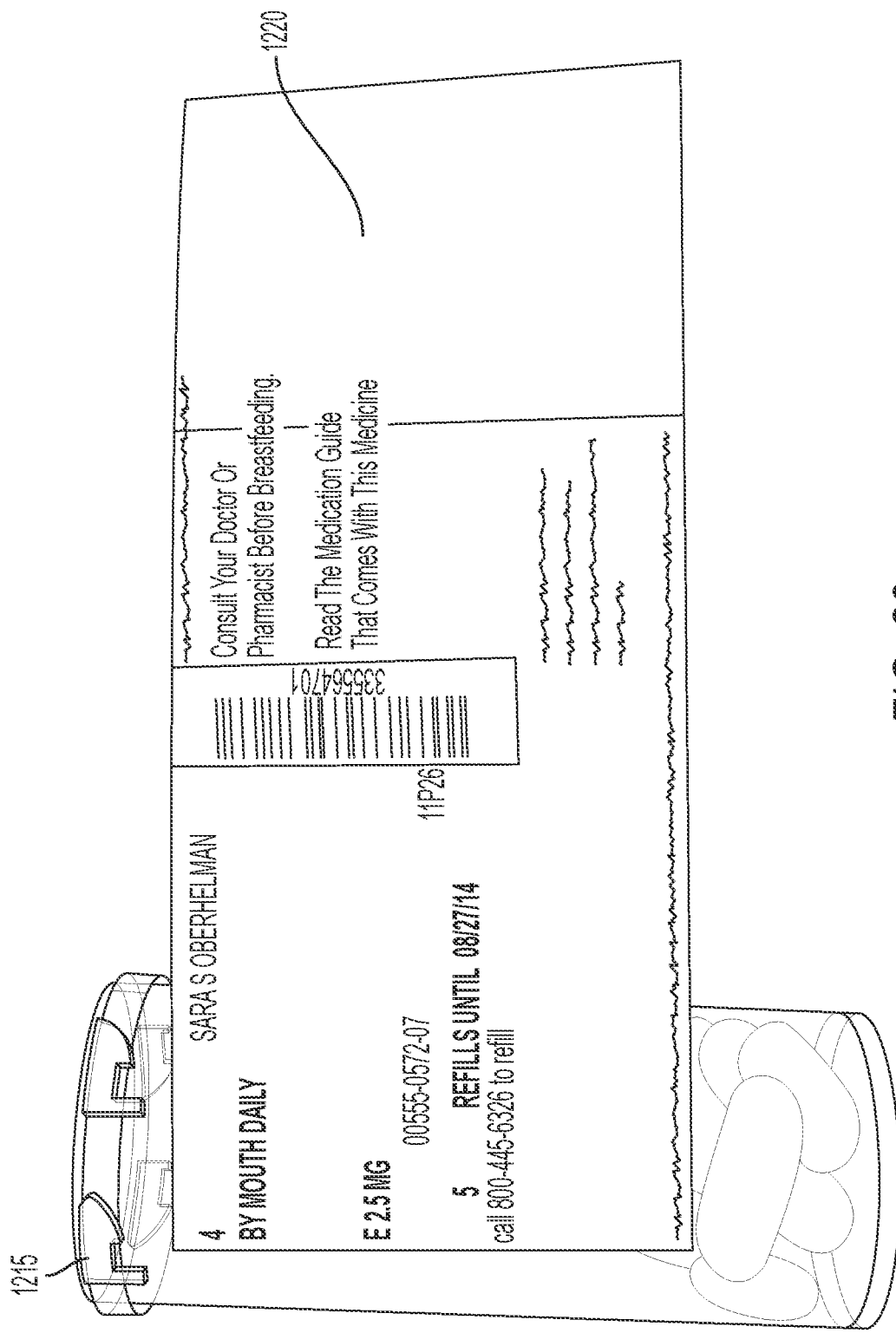
FIG. 26 illustrates an example image captured by a camera system of the pharmaceutical counting device of FIG. 10 in accordance with some embodiments.

In some embodiments, the method 1050 also includes affixing a label on the package and capturing, using the camera system a third image of the label. A technician or pharmacist may affix a label to the package (for example, the pill vial). The package may be adjusted on the tray 830 such that the label is within the view of the display device camera. The counter electronic processor 510 controls the display device camera to capture an image of the label affixed to the package. The counter electronic processor 510 stores the third image as part of the transaction record as described above. One example of the third image is shown in FIG. 26. As shown in FIG. 26, the second image illustrates a label 1220 affixed to the vial 1215. In the illustrated embodiment, the second image is taken when the label 1220 is only partially adhered to the vial 1215 so the label 1220 sticks out from the vial 1215 (like a flag), but remains planar. In other embodiments, the second image may be taken when the label 1220 is fully adhered to the vial 1215 such that the label 1220 wraps around the vial 1215. In such embodiments, multiple cameras may be used to take pictures of the vial 1215 and the label 1220 from multiple angles, and then the images may be combined using known techniques to create a composite image of a flat label. Alternatively, a user may slowly rotate the vial 1215 and the label 1220 in front of the display device camera to expose the entire label 1220 to the camera system.

Figure 23:
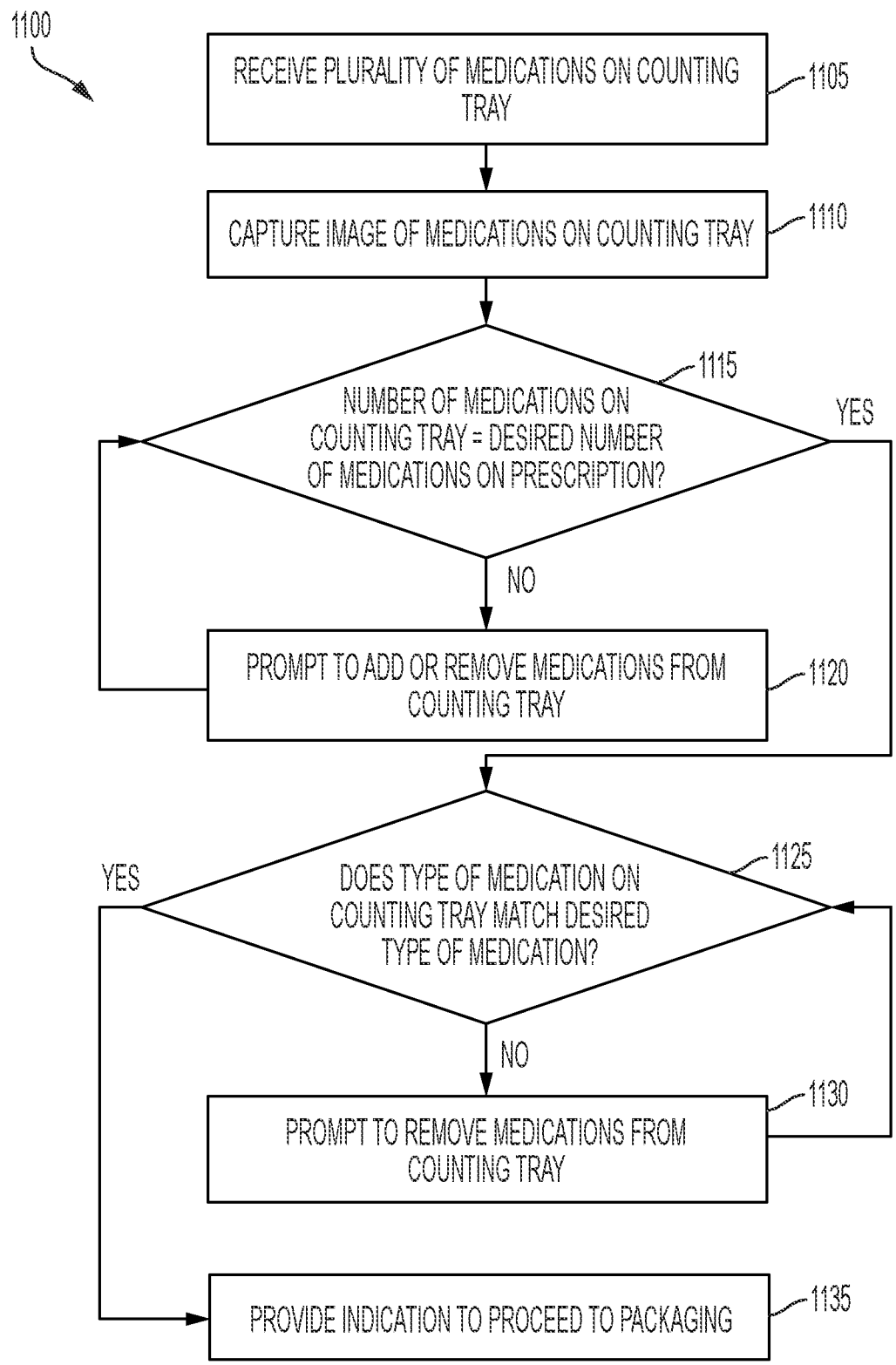
FIG. 23 is a flowchart of a method for packaging medications using the pharmaceutical counting device of FIG. 10 in accordance with some embodiments.

FIG. 23 depicts a method 1100 for packaging medications using the pharmaceutical counting device 800. Although the method 1100 includes specific blocks, all the blocks need not be performed or performed in the order presented. At block 1105, the method 1100 includes receiving a plurality of medications from the one or more bulk containers on the tray 830. The pharmacist or technician may pour the medications from a bulk container onto the tray 830 for counting. The bulk container may first be scanned using the bar code sensor 840 to verify that the type of medication within the bulk container matches a type of medication on the prescription. The pharmaceutical counting device 800 provides an indication on the display device 855 of whether the bulk container includes the correct type of medication.

At block 1110, the method includes capturing, using the camera system 950, an image of the medications on the tray 830. The counter electronic processor 510 controls the top camera 842 to capture an image of the contents of the tray 830 when the counter electronic processor 510 determines that medications are received on the tray 830. In some embodiments, the method 1050 also includes displaying, on the display device 55, the captured image of the medications on the tray and overlaying, using the counter electronic processor 510, a plurality of indications on the first image displayed on the display device to facilitate counting of a number of medications. The overlaid indications may group the medications on the tray using color codes. For example, each group of three pills may be assigned a different color, which is overlaid on the group of pills with a first group of three pills overlaid with a first color and a second group of three pills overlaid with a second color. One example of the overlaid image is illustrated in FIG. 27. As shown in FIG. 27, the overlaid image illustrates the medications 1200 on the tray 830. A grouping indicator 1225 is provided around a group of ten medications 1200 to facilitate manual counting of the medications 1200.

At block 1115, the method 1100 includes determining whether a number of medications on the tray 830 matches a desired number of medications provided on a prescription being filled by the pharmaceutical counting device 800 based on the captured image. As discussed above, the pharmacy management system 100 receives a prescription to be filled. The pharmacy management system 100 provides the information regarding the prescription including the types of medications and the number of medications for each type of medications to be filled for the prescription to the pharmacy counting device 800. The counter electronic processor 510 analyzes the captured image of the contents of the tray 830 to count the number of medications on the tray 830. Specifically, the electronic processor 510 uses image recognition techniques to determine objects in the image and identifies the number of objects in the image to determine the number of medications on the tray 830. The counter electronic processor 510 compares the number of medications on the tray 830 to the desired number of medications to determine whether the number of medications on the tray 830 matches the desired number of medications.

At block 1120, the method 1100 includes prompting, using the display device 855, to add or remove medications from the tray 830 when the number of medications on the tray 830 does not match the desired number of medications. In one example, the prompt may show the current count of pharmaceuticals on the display device 855 overlaid on a color coded indications. When the correct number of medications are received on the tray 830, the indication may include a green circle with a check mark in the middle. When the incorrect number of medications are received on the tray 830, the indication may include a red circle with the count in the middle.

At block 1125, the method 1100 includes determining whether a type of medication on the tray 830 matches a desired type of medication provided on the prescription based on the captured image. The counter electronic processor 510 analyzes the captured image of the contents of the tray 830 to determine the type of medication on the tray. Specifically, the counter electronic processor 510 uses image recognition techniques to determine object in the image. The counter electronic processor 510 then extracts characteristics of the objects, for example, a size (e.g., diameter, length, width, and the like), a shape, a color, indications on the object, and/or the like. The counter electronic processor 510 then compares the characteristics of each medication with the characteristics of the desired medication. The characteristics of the desired medications may be obtained from the national drug code (NDC) database. In some embodiments, the characteristics of the desired medications are obtained using training data. That is, the counter electronic processor 510 learns the characteristics of the medications as the medications are being counted using the pharmaceutical counting device 800. The counter electronic processor 510 compares the characteristics of the medication on the tray 830 to the characteristics of the expected type of medication to determine whether the type of medication on the tray 830 matches the desired type of medication. The counter electronic processor 510 may also determine if partial or broken medications or other debris are on the tray 830.

At block 1130, the method 1100 includes prompting, using the display device 855, to remove medications from the tray 830 when the type of medication on the counting tray does not match the desired type of medication. In one example, the prompt may include a color-coded image on the display device pointing to the medications that are of the incorrect type. For example, the captured image may be displayed with all the medications that match the correct type highlighted in green and all the medications that do not match the correct type highlighted in red. One example of the indications is illustrated in FIG. 24. FIG. 24 shows an image captured of the tray 830 which may be displayed on the display device 855. The image illustrates the medications 1200, with a highlight 1205 around the medications 1200 showing whether or not the medications is of the correct type (that is, matches the type of medication currently being packaged). This allows the user to immediately determine which of the medications to remove the tray 830.

At block 1140, the method 1100 includes providing, using the display device 855, an indication to proceed to packaging when the number of medications on the tray 830 matches the desired number of medications and the type of medication on the tray 830 matches the desired type of medication. For example, the display device 855 provides a green circle with a check mark to indicate that the correct number and type of medications are included on the tray 830.

One advantage of the above methods is that a pharmacist is provided with two opportunities to ensure the prescription is accurately filled. Additionally, the above methods leverage the automated pharmacy to efficiently package pharmaceuticals such that customer wait times are reduced.

Various features and advantages of the invention are set forth in the following claims.

The invention claimed is:

1. A method for packaging medications using a pharmaceutical counting device including a counting tray configured to receive medications, the method comprising:
   receiving, at a pharmacy management system, a prescription to be filled;
   receiving a plurality of medications from one or more bulk containers on the counting tray;
   determining, using an electronic processor of the pharmaceutical counting device, that a correct number of medications to fill the prescription is received on the counting tray;
   capturing, using a camera system of the pharmaceutical counting device, a first image of the correct number of medications on the counting tray;
   capturing, using the camera system, a second image of package including packaged medications, wherein the correct number of medications on the counting tray is packaged into the package; and generating, using the electronic processor, a transaction record corresponding to filling the prescription including the first image and the second image.

2. The method of claim 1, further comprising:

capturing, using the camera system, a third image of a label affixed to the package, wherein the transaction record further includes the third image.

3. The method of claim 1, further comprising:

displaying, on a display device of the pharmaceutical counting device, the first image; and overlaying, using the electronic processor, a plurality of indications on the first image displayed on the display device to facilitate manual counting of a number of medications.

4. The method of claim 1, further comprising:

determining, using the electronic processor, an expected medication type to be counted using the pharmaceutical counting device; and prompting, using a display of the pharmaceutical counting device, to remove medications from the counting tray when the medications on the counting tray do not match the expected medication type.

5. A pharmaceutical counting device comprising:

a base portion;

a counting tray provided on the base portion and configured to receive medications for counting;

a camera system including a camera positioned above the counting tray and configured to capture an image of contents of the counting tray; and an electronic processor coupled to the camera system and configured to receive a prescription to be filled;

determine, using the camera system, that a correct number of medications to fill the prescription is received on the counting tray;

capture, using the camera system, a first image of the correct number of medications on the counting tray;

capture, using the camera system, a second image of a package including packaged medications, wherein the correct number of medications on the counting tray is packaged into the package; and generate a transaction record corresponding to filling the prescription including the first image and the second image.

6. The pharmaceutical counting device of claim 5, wherein the electronic processor is further configured to capture, using the camera system, a third image of a label affixed to the package, wherein the transaction record further includes the third image.

7. The pharmaceutical counting device of claim 5, further comprising a display device, wherein the electronic processor is coupled to the display device and is further configured to display, on the display device, the first image; and overlay a plurality of indications on the first image displayed on the display device to facilitate manual counting of a number of medications.

8. The pharmaceutical counting device of claim 5, further comprising a display device, wherein the electronic processor is further configured to determine an expected medication type to be counted using the pharmaceutical counting device; and prompt, using the display device, to remove medications from the counting tray when the medications on the counting tray do not match the expected medication type.

* * * * *